US007801610B2

(12) United States Patent
Bohn et al.

(10) Patent No.: US 7,801,610 B2
(45) Date of Patent: Sep. 21, 2010

(54) METHODS AND SYSTEMS FOR MANAGEMENT OF ATRIAL RETROGRADE CONDUCTION AND PACEMAKER MEDIATED TACHYARRHYTHMIA

(75) Inventors: Derek D. Bohn, Woodbury, MN (US); Ankur Garg, Minneapolis, MN (US); Eric K. Enrooth, Lino Lakes, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 412 days.

(21) Appl. No.: 11/601,092

(22) Filed: Nov. 17, 2006

(65) Prior Publication Data

US 2008/0119902 A1    May 22, 2008

(51) Int. Cl.
*A61N 1/362* (2006.01)
(52) U.S. Cl. .............................. 607/28; 607/9; 607/14; 607/27
(58) Field of Classification Search .................. 607/9, 607/14, 27, 28
See application file for complete search history.

(56) References Cited

U.S. PATENT DOCUMENTS

| 4,505,276 A | 3/1985 | Markowitz et al. |
| 4,543,963 A | 10/1985 | Gessman |
| 4,569,350 A | 2/1986 | Mumford et al. |
| 5,000,189 A | 3/1991 | Throne et al. |
| 5,139,028 A | 8/1992 | Steinhaus et al. |
| 5,217,021 A | 6/1993 | Steinhaus et al. |
| 5,253,644 A | 10/1993 | Elmvist |
| 5,273,035 A | 12/1993 | Markowitz et al. |
| 5,312,450 A | 5/1994 | Markowitz |
| 5,350,410 A | 9/1994 | Kleks et al. |
| 5,374,280 A | 12/1994 | den Dulk |
| 5,383,910 A | 1/1995 | Den Dulk |
| 5,447,519 A | 9/1995 | Peterson |
| 5,458,623 A | 10/1995 | Lu et al. |

(Continued)

FOREIGN PATENT DOCUMENTS

EP    1116494    7/2001

(Continued)

OTHER PUBLICATIONS

Restriction from U.S. Appl. No. 11/601,217 dated Mar. 12, 2010, 6 pages.

(Continued)

*Primary Examiner*—Carl H Layno
*Assistant Examiner*—Pamela M Bays
(74) *Attorney, Agent, or Firm*—Hollingworth & Funk, LLC

(57) ABSTRACT

Methods and systems for classifying cardiac responses to pacing stimulation and managing retrograde conduction and pacemaker mediated tachyarrhythmia are described. An atrial pacing pulse and a ventricular pacing pulse are delivered during a paced cardiac cycle. A post ventricular atrial refractory period (PVARP) is timed following the ventricular pacing pulse. The system determines if the atrial pacing pulse captures the atrium. An atrial depolarization occurring after the paced cardiac cycle is sensed. Retrograde management is initiated if the atrial pacing pulse did not capture the atrium and the atrial depolarization occurred during the PVARP. Pacemaker mediated tachyarrhythmia (PMT) is initiated if the atrial pacing pulse did not capture the atrium and the atrial depolarization did not occur during the PVARP.

13 Claims, 15 Drawing Sheets

U.S. PATENT DOCUMENTS

| | | | |
|---|---|---|---|
| 5,476,482 A | 12/1995 | Lu | |
| 5,534,017 A | 7/1996 | Van Krieken et al. | |
| 5,549,648 A | 8/1996 | Stoop | |
| 5,601,615 A | 2/1997 | Markowitz et al. | |
| 5,653,738 A * | 8/1997 | Sholder | 607/14 |
| 5,683,431 A | 11/1997 | Wang | |
| 5,713,933 A | 2/1998 | Condie et al. | |
| 5,766,229 A | 6/1998 | Bornzin | |
| 5,779,645 A | 7/1998 | Olson et al. | |
| 5,817,027 A | 10/1998 | Arand et al. | |
| 5,843,137 A | 12/1998 | Condie et al. | |
| 5,857,977 A | 1/1999 | Caswell et al. | |
| 5,871,509 A | 2/1999 | Noren | |
| 6,038,474 A | 3/2000 | Zhu et al. | |
| 6,052,620 A | 4/2000 | Gillberg et al. | |
| 6,076,014 A | 6/2000 | Alt | |
| 6,101,416 A | 8/2000 | Sloman | |
| 6,128,535 A | 10/2000 | Maarse | |
| 6,163,724 A | 12/2000 | Hemming et al. | |
| 6,167,307 A | 12/2000 | Hess | |
| 6,175,766 B1 | 1/2001 | Bornzin et al. | |
| 6,221,011 B1 | 4/2001 | Bardy | |
| 6,259,950 B1 | 7/2001 | Mann et al. | |
| 6,270,457 B1 | 8/2001 | Bardy | |
| 6,275,731 B1 | 8/2001 | Zhu et al. | |
| 6,277,072 B1 | 8/2001 | Bardy | |
| 6,280,380 B1 | 8/2001 | Bardy | |
| 6,312,378 B1 | 11/2001 | Bardy | |
| 6,336,903 B1 | 1/2002 | Bardy | |
| 6,358,203 B2 | 3/2002 | Bardy | |
| 6,363,281 B1 | 3/2002 | Zhu et al. | |
| 6,368,284 B1 | 4/2002 | Bardy | |
| 6,389,316 B1 | 5/2002 | Bornzin et al. | |
| 6,398,728 B1 | 6/2002 | Bardy | |
| 6,408,210 B1 | 6/2002 | Bornzin et al. | |
| 6,418,343 B1 | 7/2002 | Zhang et al. | |
| 6,440,066 B1 | 8/2002 | Bardy | |
| 6,449,503 B1 | 9/2002 | Hsu | |
| 6,456,881 B1 | 9/2002 | Bornzin et al. | |
| 6,473,649 B1 | 10/2002 | Gryzwa et al. | |
| 6,496,730 B1 | 12/2002 | Kleckner et al. | |
| 6,498,949 B2 | 12/2002 | Levine et al. | |
| 6,505,070 B1 | 1/2003 | Backers | |
| 6,505,071 B1 | 1/2003 | Zhu et al. | |
| 6,587,723 B1 * | 7/2003 | Sloman et al. | 607/28 |
| 6,609,028 B2 | 8/2003 | Struble | |
| 6,611,714 B1 | 8/2003 | Mo | |
| 6,618,622 B1 | 9/2003 | Mann et al. | |
| 6,625,489 B2 | 9/2003 | Sheth et al. | |
| 6,643,549 B1 | 11/2003 | Bradley et al. | |
| 6,684,100 B1 | 1/2004 | Sweeney et al. | |
| 6,697,673 B1 | 2/2004 | Lu | |
| 6,721,601 B1 | 4/2004 | Bornzin et al. | |
| 6,768,924 B2 | 7/2004 | Ding et al. | |
| 6,925,326 B1 | 8/2005 | Levine et al. | |
| 6,950,704 B1 | 9/2005 | Bradley | |
| 7,006,869 B2 | 2/2006 | Bradley | |
| 7,072,714 B2 | 7/2006 | Busch et al. | |
| 7,076,290 B2 | 7/2006 | Sheth et al. | |
| 7,076,297 B2 | 7/2006 | Limousin et al. | |
| 7,123,954 B2 | 10/2006 | Narayan et al. | |
| 7,130,685 B2 | 10/2006 | Casavant et al. | |
| 7,130,690 B2 | 10/2006 | Rueter et al. | |
| 7,133,718 B2 | 11/2006 | Bakken et al. | |
| 7,177,685 B2 | 2/2007 | Lincoln et al. | |
| 7,319,900 B2 | 1/2008 | Kim et al. | |
| 7,324,848 B1 | 1/2008 | Turcott | |
| 7,330,761 B2 | 2/2008 | Zhang et al. | |
| 7,457,666 B2 | 11/2008 | Bohn et al. | |
| 7,509,168 B1 * | 3/2009 | Mengotto et al. | 607/14 |
| 2003/0125777 A1 | 7/2003 | Ding et al. | |
| 2004/0260348 A1 | 12/2004 | Bakken et al. | |
| 2005/0021095 A1 * | 1/2005 | Rueter et al. | 607/9 |
| 2005/0080347 A1 | 4/2005 | Sheth et al. | |
| 2005/0131476 A1 | 6/2005 | Kim et al. | |
| 2005/0131477 A1 | 6/2005 | Meyer et al. | |
| 2005/0131478 A1 | 6/2005 | Kim et al. | |
| 2006/0129197 A1 | 6/2006 | Zhang et al. | |
| 2006/0129198 A1 | 6/2006 | Zhang et al. | |
| 2006/0129199 A1 | 6/2006 | Zhang et al. | |
| 2006/0247693 A1 | 11/2006 | Dong et al. | |

FOREIGN PATENT DOCUMENTS

| | | |
|---|---|---|
| WO | WO2006065707 | 6/2006 |

OTHER PUBLICATIONS

Office Action from U.S. Appl. No. 11/012,692 dated Aug. 27, 2007, 6 pages.

Office Action from U.S. Appl. No. 11/012,692 dated Dec. 3, 2007, 9 pages.

Office Action from U.S. Appl. No. 11/012,692 dated Aug. 25, 2008, 12 pages.

Examiner's Answer from U.S. Appl. No. 11/012,692 dated Mar. 12, 2009, 12 pages.

Office Action Response from U.S. Appl. No. 11/012,692 dated Sep. 24, 2007, 6 pages.

Office Action Response from U.S. Appl. No. 11/012,692 dated Jun. 2, 2008, 8 pages.

Appeal Brief from U.S. Appl. No. 11/012,692 dated Dec. 8, 2008, 25 pages.

Reply Brief from U.S. Appl. No. 11/012,692 dated May 5, 2009, 9 pages.

International Search Report and Written Opinion from PCT Application No. PCT/US2007/023820 dated Apr. 15, 2008, 13 pages.

International Preliminary Report on Patentability from PCT Application No. PCT/US2007/023820 dated May 28, 2009, 5 pages.

* cited by examiner

METHODS AND SYSTEMS FOR MANAGEMENT OF ATRIAL RETROGRADE CONDUCTION AND PACEMAKER MEDIATED TACHYARRHYTHMIA

RELATED PATENT DOCUMENT

This patent application is related to commonly owned U.S. patent application Ser. No. 11/601,217, entitled "DYNAMIC MORPHOLOGY BASED ATRIAL AUTOMATIC THRESHOLD," filed concurrently herewith and incorporated herein by reference.

FIELD OF THE INVENTION

The present invention relates generally to implantable medical devices and, more particularly, to atrial pacing.

BACKGROUND OF THE INVENTION

When functioning normally, the heart produces rhythmic contractions and is capable of efficiently pumping blood throughout the body. However, due to disease or injury, the heart rhythm may become irregular resulting in diminished pumping efficiency.

Arrhythmia is a general term used to describe heart rhythm irregularities arising from a variety of physical conditions and disease processes. Cardiac rhythm management systems, such as implantable pacemakers and cardiac defibrillators, have been used as an effective treatment for patients with serious arrhythmias. These systems typically include circuitry to sense electrical signals from the heart and a pulse generator for delivering electrical stimulation pulses to the heart. Leads extending into the patient's heart are connected to electrodes that contact the myocardium for sensing the heart's electrical signals and for delivering stimulation pulses to the heart in accordance with various therapies.

Cardiac rhythm management systems operate to stimulate the heart tissue adjacent to the electrodes to produce a contraction of the tissue. Pacemakers are cardiac rhythm management systems that deliver a series of low energy pace pulses timed to assist the heart in producing a contractile rhythm that maintains cardiac pumping efficiency. Pace pulses may be intermittent or continuous, depending on the needs of the patient. There exist a number of categories of pacemaker devices, with various modes for sensing and pacing one or more heart chambers.

When a pace pulse produces a contraction in the heart tissue, the electrical cardiac signal following the contraction is denoted the evoked response (ER) signal. Superimposed on the evoked response signal is a signal associated with residual post pace polarization at the electrode-tissue interface. The magnitude of the residual post pace polarization signal, or pacing artifact, may be affected by a variety of factors including lead polarization, after-potential from the pace pulse, lead impedance, patient impedance, pace pulse width, and pace pulse amplitude, for example. The post pace polarization signal is present whether or not the pace captures the heart tissue.

A pace pulse must exceed a minimum energy value, or capture threshold, to produce a contraction. It is desirable for a pace pulse to have sufficient energy to stimulate capture of the heart without expending energy significantly in excess of the capture threshold. Thus, accurate determination of the capture threshold may be required for efficient pace energy management. If the pace pulse energy is too low, the pace pulses may not reliably produce a contractile response in the heart and may result in ineffective pacing. If the pace pulse energy is too high, the patient may experience discomfort and the battery life of the device will be shorter.

Capture detection allows the cardiac rhythm management system to adjust the energy level of pace pulses to correspond to the optimum energy expenditure that reliably produces a contraction. Further, capture detection allows the cardiac rhythm management system to initiate a back-up pulse at a higher energy level whenever a pace pulse does not produce a contraction.

Retrograde conduction may occur, for example, when a depolarization wave initiated in a ventricle by a pacing pulse or intrinsic activation of the ventricle travels back to the atrium producing a retrograde P-wave. Retrograde P-waves may inhibit effective atrial pacing. A pacing pulse delivered to the atrium will not result in capture if the atrial tissue is refractory due to a retrograde P-wave. Further, retrograde conduction to the atrium may cause pacemaker mediated tachyarrhythmia (PMT).

There is a need for methods and systems that reliably determine if a pacing pulse captures an atrium. There is a further need for methods and systems that provide atrial retrograde management and PMT management during atrial pacing. The present invention fulfills these and other needs.

SUMMARY OF THE INVENTION

Embodiments of the present invention are directed to methods and systems for retrograde management and PMT management during atrial pacing. One embodiment is directed to a method for initiating retrograde and PMT management. An atrial pacing pulse and a ventricular pacing pulse are delivered during a paced cardiac cycle. A post ventricular atrial refractory period (PVARP) is timed following the ventricular pacing pulse. The system determines if the atrial pacing pulse captures the atrium. An atrial depolarization occurring after the paced cardiac cycle is sensed. Retrograde management is initiated if the atrial pacing pulse did not capture the atrium and the atrial depolarization occurred during the PVARP. Pacemaker mediated tachyarrhythmia (PMT) is initiated if the atrial pacing pulse did not capture the atrium and the atrial depolarization did not occur during the PVARP. For example the atrial depolarization may comprise a retrogradely conducted depolarization responsive to the ventricular pacing pulse or a premature atrial contraction.

According to one aspect of the invention, initiating retrograde management involves modifying pacing for at least one pacing cycle. In another aspect, initiating the retrograde management involves delaying a next scheduled atrial pacing pulse following the paced cardiac cycle. According to yet another aspect, initiating the retrograde management involves delaying a next scheduled atrial pacing pulse if the next scheduled atrial pacing pulse is scheduled to occur when the atrial tissue is refractory. For example, the next scheduled atrial pacing pulse may be delayed until about 300 ms from the atrial depolarization.

In some implementations, initiating the PMT management involves extending a subsequent PVARP of at least one pacing cycle occurring after the paced cardiac cycle. In some implementations, initiating the PMT management comprises extending a subsequent PVARP of a next pacing cycle occurring after the paced cardiac cycle. For example, the subsequent PVARP may be extended about 500 ms.

Another embodiment of the invention is directed to a cardiac rhythm management system. The cardiac rhythm management system includes a pulse generator configured to deliver an atrial pacing pulse and a ventricular pacing pulse via electrodes coupled to a heart during a paced cardiac cycle. A post ventricular atrial refractory period (PVARP) timer times a PVARP following the ventricular pacing pulse. A capture detector determines if the atrial pacing pulse captures the atrium. A sensing system configured to senses an atrial depolarization that occurs after the paced cardiac cycle. A retrograde management module initiates retrograde management pacing if the atrial pacing pulse did not capture the atrium and the atrial depolarization occurred during the PVARP. A pacemaker mediated tachyarrhythmia (PMT) management module initiates PMT management if the atrial pacing pulse did not capture the atrium and the atrial depolarization did not occur during the PVARP. The atrial depolarization may comprise, for example a retrogradely conducted depolarization responsive to the ventricular pacing pulse or a premature contraction.

In some implementations, the retrograde management module is configured to delay a next scheduled atrial pacing pulse following the paced cardiac cycle to initiate retrograde management. In some implementations, the retrograde management module is configured to delay a next scheduled atrial pacing pulse if the next scheduled atrial pacing pulse is scheduled to occur when the tissue is refractory. For example, the retrograde management module is configured to delay the next schedule atrial pacing pulse until about 300 ms from the atrial depolarization.

The PMT management module is configured to extend a subsequent PVARP of a next pacing cycle occurring after the paced cardiac cycle. For example, the subsequent PVARP may be extended to about 500 ms.

The above summary of the present invention is not intended to describe each embodiment or every implementation of the present invention. Advantages and attainments, together with a more complete understanding of the invention, will become apparent and appreciated by referring to the following detailed description and claims in conjunction with the accompanying drawings.

Figure 1:
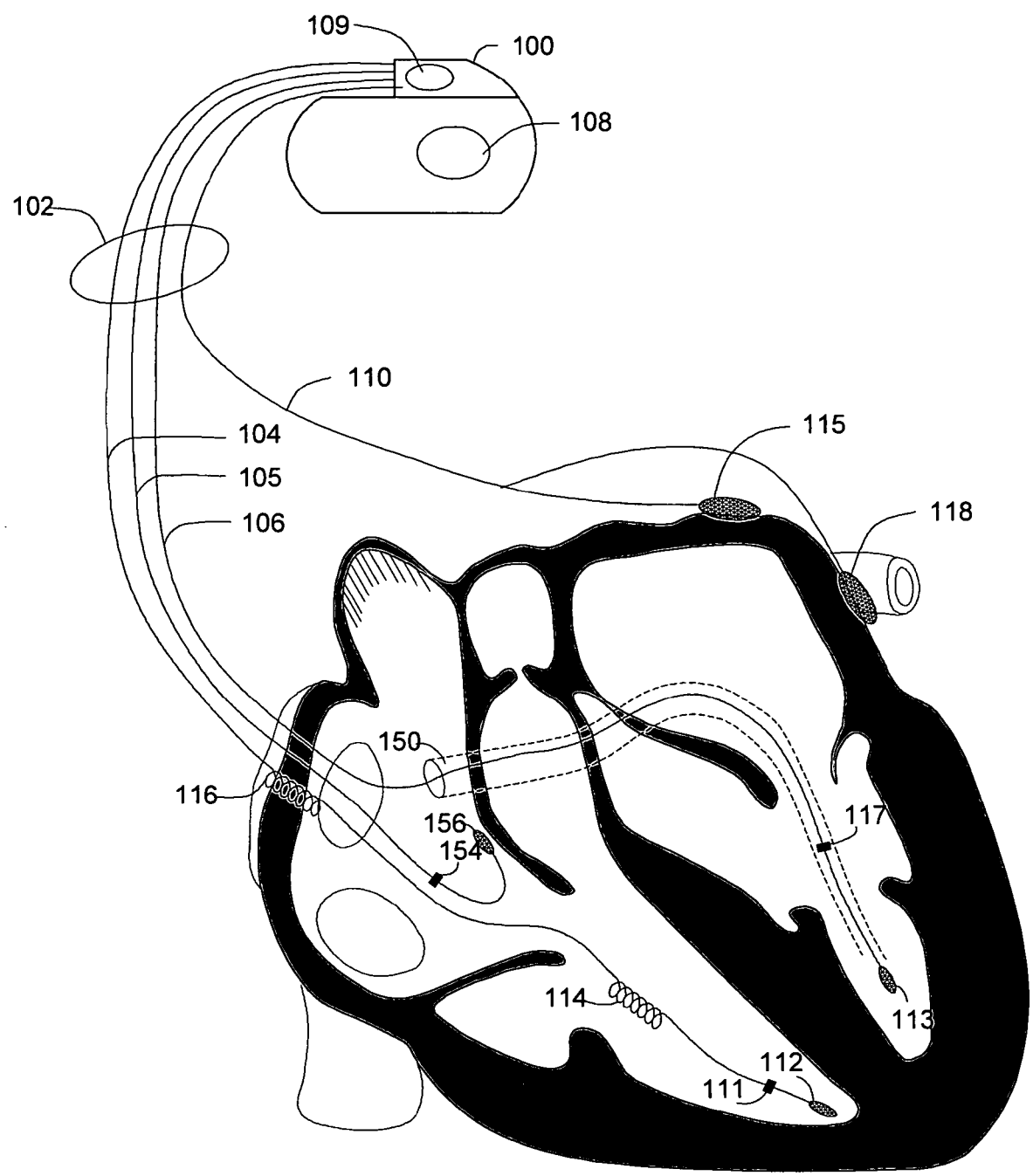
FIG. 1 illustrates an implantable cardiac rhythm management (CRM) system that may be used in connection with atrial pacing methods in accordance with embodiments of the invention.

While the invention is amenable to various modifications and alternative forms, specifics thereof have been shown by way of example in the drawings and will be described in detail below. It is to be understood, however, that the intention is not to limit the invention to the particular embodiments described. On the contrary, the invention is intended to cover all modifications, equivalents, and alternatives falling within the scope of the invention as defined by the appended claims.

DETAILED DESCRIPTION OF VARIOUS EMBODIMENTS

In the following description of the illustrated embodiments, references are made to the accompanying drawings forming a part hereof, and in which are shown, by way of illustration, various embodiments by which the invention may be practiced. It is to be understood that other embodiments may be utilized, and structural and functional changes may be made without departing from the scope of the present invention.

Systems, devices or methods according to the present invention may include one or more of the features, structures, methods, or combinations thereof described herein. For example, a device or system may be implemented to include one or more of the advantageous features and/or processes described below. It is intended that such device or system need not include all of the features described herein, but may be implemented to include selected features that provide for useful structures and/or functionality. Such a device or system may be implemented to provide a variety of therapeutic or diagnostic functions.

After delivery of a pacing pulse to a heart chamber, various cardiac responses to the pacing pulse are possible. In one scenario, the pacing pulse may generate a propagating wavefront of depolarization resulting in a contraction of the heart chamber. In this scenario, the pacing pulse is said to have captured the heart chamber. Capture of the heart chamber may occur if the pacing pulse has sufficient energy and is delivered during a non-refractory period. If the pacing pulse does not produce contraction of the chamber, the cardiac response is referred to as non-capture or loss of capture. Non-capture may occur, for example, if the pacing pulse energy is too low, and/or if the pacing pulse is delivered during a refractory period of the cardiac tissue. Fusion occurs when a depolarization initiated by a pace merges with an intrinsic depolarization.

Approaches for determining pacing response described herein rely on consistency in the morphology of the cardiac signal sensed following a pacing pulse to discriminate between noncapture, capture, and fusion responses. The approaches described herein are particularly advantageous when used for atrial pacing response classification in conjunction with retrograde conduction management and/or PMT management. One or more features of the sensed cardiac signal following pacing, e.g., peak magnitude and peak timing, may be analyzed with respect to feature thresholds and/or timing intervals to determine the pacing response.

Pacing response classification such as by the methods described herein may be used with or without retrograde conduction management and/or PMT management. If noncapture occurs, retrograde conduction from an intrinsic or paced ventricular depolarization may cause a false noncapture detection on the next pacing cycle. Retrograde conduction during capture threshold testing, for example, may lead to erroneous capture threshold determination. Retrograde conduction may also cause undesirable fast pacing, denoted pacemaker mediated tachyarrhythmia (PMT). Some embodiments described herein include methods and systems that provide for management of retrograde conduction and PMT.

By way of example, the processes of the present invention may be used in capture threshold testing to determine the optimal energy for pacing. Capture detection allows the cardiac rhythm management system to adjust the energy level of pace pulses to correspond to the optimum energy expenditure that reliably produces a contraction. Embodiments of the present invention are directed to methods and systems for pacing response classification to distinguish between capture, noncapture, and fusion based on atrial evoked response sensing in an implantable pacemaker, defibrillator or cardiac resynchronization therapy device. The pacing response classification processes described herein are based on the use of timing windows and multiple amplitude thresholds to translate atrial evoked response peak amplitude and timing information into capture, noncapture and fusion response classification.

Noncapture of the atrium by an atrial pace may allow retrograde conduction to occur when a depolarization wave initiated in a ventricle by a pacing pulse or intrinsic activation of the ventricle travels back to the atrium producing a retrograde P-wave. A pacing pulse delivered to the atrium will not result in capture if the atrial tissue is refractory due to a retrograde P-wave. Retrograde P-waves may inhibit accurate determination of the capture threshold during a capture threshold test. Further, retrograde conduction to the atrium may cause pacemaker mediated tachycardia (PMT). Embodiments of the invention are directed to methods and systems for managing atrial retrograde conduction and PMT.

Those skilled in the art will appreciate that reference to a capture threshold testing procedure indicates a method of determining the capture threshold in one or more of the left atrium, right atrium, left ventricle, and right ventricle. In such a procedure, the pacemaker, automatically or upon command, initiates a search for the capture threshold of the selected heart chamber. The capture threshold is defined as the lowest pacing energy that consistently captures the heart.

In one example of an automatic capture threshold procedure, the pacemaker delivers a sequence of pacing pulses to the heart and detects the cardiac pacing responses to the pace pulses. The energy of the pacing pulses may be decreased in discrete steps until a predetermined number of noncapture responses occur. The pacemaker may increase the stimulation energy in discrete steps until a predetermined number of capture responses occur to confirm the capture threshold. A capture threshold test may be performed using pacing response classification, retrograde management, and/or PMT management methods of the present invention.

Other procedures for implementing capture threshold testing may be utilized. In one example, the pacing energy may be increased in discrete steps until capture is detected. In another example, the pacing energy may be adjusted according to a binomial search pattern, or other search patterns.

Capture threshold determination is distinguishable from automatic capture detection, a procedure that typically occurs on a beat-by-beat basis during pacing. Automatic capture detection verifies that a delivered pace pulse results in a captured response. When a captured response is not detected following a pace pulse, the pacemaker may deliver a back up safety pace to ensure consistent pacing. If back up pacing is implemented, the back up pace may be delivered, for example, about 70-80 ms after the initial pace pulse. If a predetermined number of pace pulses delivered during normal pacing do not produce a captured response, the pacemaker may initiate a capture threshold test to determine the capture threshold. Alternatively, if a predetermined number of pacing pulses do not produce a captured response, the pacemaker may adjust the pacing energy for the next pacing pulse. Pacing response classification, retrograde management, and/or PMT management may be implemented in conjunction with capture verification and/or capture threshold testing using processes of the present invention.

Referring now to FIG. 1 of the drawings, there is shown a cardiac rhythm management (CRM) system that may be used to implement discrimination between capture, noncapture, and fusion and/or to provide retrograde management and/or PMT management in accordance with the approaches of the present invention. The CRM system in FIG. 1 includes a an implantable cardiac device (ICD) 100 such as a device incorporating the functions of a pacemaker, pacemaker/defibrillator, or cardiac resynchronization therapy (CRT) device, enclosed within a housing and coupled to a lead system 102. The housing and/or header of the ICD 100 may incorporate one or more can or indifferent electrodes 108, 109 used to provide electrical stimulation energy to the heart and/or to sense cardiac electrical activity. The ICD 100 may utilize all or a portion of the pacemaker housing as a can electrode 108. The ICD 100 may include an indifferent electrode 109 positioned, for example, on the header or the housing of the pacemaker 100. If the pacemaker 100 includes both a can electrode 108 and an indifferent electrode 109, the electrodes 108, 109 typically are electrically isolated from each other.

The lead system 102 is used to detect cardiac electrical signals produced by the heart and to provide electrical energy to the heart under certain predetermined conditions to treat cardiac arrhythmias. The lead system 102 may include one or more electrodes used for pacing, sensing, and/or defibrillation. In the embodiment shown in FIG. 1, the lead system 102 includes an intracardiac right ventricular (RV) lead system 104, an intracardiac right atrial (RA) lead system 105, and an intracardiac left ventricular (LV) lead system 106. An extracardiac left atrial (LA) lead system 110 is employed in this example.

The CRM system illustrated in FIG. 1 is configured for biventricular and/or biatrial pacing. The lead system 102 illustrates one embodiment that may be used in connection with the capture detection processes described herein. Other leads and/or electrodes may additionally or alternatively be used. For example, the CRM system may pace multiple sites in one cardiac chamber via multiple electrodes within the chamber. This type of multisite pacing may be employed in one or more of the right atrium, left atrium, right ventricle or left ventricle. Multisite pacing in a chamber may be used for example, to increase the power and/or synchrony of cardiac contractions of the paced chamber.

The lead system 102 may include intracardiac leads 104, 105, 106 implanted in a human body with portions of the intracardiac leads 104, 105, 106 inserted into a heart. The intracardiac leads 104, 105, 106 include various electrodes positionable within the heart for sensing electrical activity of the heart and for delivering electrical stimulation energy to the heart, for example, pacing pulses and/or defibrillation shocks to treat various arrhythmias of the heart.

As illustrated in FIG. 1, the lead system 102 may include one or more extracardiac leads 110 having electrodes 115, 118, e.g., epicardial electrodes, positioned at locations outside the heart for sensing and pacing one or more heart chambers. In some configurations, the epicardial electrodes may be placed on or about the outside of the heart and/or embedded in the myocardium from locations outside the heart.

The right ventricular lead system 104 illustrated in FIG. 1 includes an SVC-coil 116, an RV-coil 114, an RV-ring electrode 111, and an RV-tip electrode 112. The right ventricular lead system 104 extends through the right atrium and into the right ventricle. In particular, the RV-tip electrode 112, RV-ring electrode 111, and RV-coil electrode 114 are positioned at appropriate locations within the right ventricle for sensing and delivering electrical stimulation pulses to the heart. The SVC-coil 116 is positioned at an appropriate location within the right atrium chamber of the heart or a major vein leading to the right atrial chamber.

In one configuration, the RV-tip electrode 112 referenced to the can electrode 108 may be used to implement unipolar pacing and/or sensing in the right ventricle. Bipolar pacing and/or sensing in the right ventricle may be implemented using the RV-tip 112 and RV-ring 111 electrodes. In yet another configuration, the RV-ring 111 electrode may optionally be omitted, and bipolar pacing and/or sensing may be accomplished using the RV-tip electrode 112 and the RV-coil 114, for example. The right ventricular lead system 104 may be configured as an integrated bipolar pace/shock lead. The RV-coil 114 and the SVC-coil 116 are defibrillation electrodes.

The left ventricular lead 106 includes an LV distal electrode 113 and an LV proximal electrode 117 located at appropriate locations in or about the left ventricle for pacing and/or sensing the left ventricle. The left ventricular lead 106 may be guided into the right atrium of the heart via the superior vena cava. From the right atrium, the left ventricular lead 106 may be deployed into the coronary sinus ostium, the opening of the coronary sinus 150. The lead 106 may be guided through the coronary sinus 150 to a coronary vein of the left ventricle. This vein is used as an access pathway for leads to reach the surfaces of the left ventricle which are not directly accessible from the right side of the heart. Lead placement for the left ventricular lead 106 may be achieved via subclavian vein access and a preformed guiding catheter for insertion of the LV electrodes 113, 117 adjacent to the left ventricle.

Unipolar pacing and/or sensing in the left ventricle may be implemented, for example, using the LV distal electrode referenced to the can electrode 108. The LV distal electrode 113 and the LV proximal electrode 117 may be used together as bipolar sense and/or pace electrodes for the left ventricle. The lead system 102 in conjunction with the ICD 100 may provide bradycardia pacing therapy to maintain a hemodynamically sufficient heart rate. The left ventricular lead 106 and the right ventricular lead 104 and/or the right atrial lead and the left atrial lead may be used to provide cardiac resynchronization therapy such that the ventricles and/or atria of the heart are paced substantially simultaneously or in phased sequence separated by an interventricular or interatrial pacing delay, to provide enhanced cardiac pumping efficiency for patients suffering from congestive heart failure.

The right atrial lead 105 includes a RA-tip electrode 156 and an RA-ring electrode 154 positioned at appropriate locations in the right atrium for sensing and pacing the right atrium. In one configuration, the RA-tip 156 referenced to the can electrode 108, for example, may be used to provide unipolar pacing and/or sensing in the right atrium. In another configuration, the RA-tip electrode 156 and the RA-ring electrode 154 may be used to effect bipolar pacing and/or sensing.

Referring now to FIG. 2A, there is shown a block diagram of an embodiment of a CRM system 200 suitable for implementing atrial pacing with cardiac response classification, retrograde management and/or PMT management according to the approaches of the present invention.

The CRM system 200 includes a control processor 240 capable of controlling the delivery of pacing pulses or defibrillation shocks to the right ventricle, left ventricle, right atrium and/or left atrium. The pacing pulse generator 230 is configured to generate pacing pulses for treating bradyarrhythmia, for example, or for synchronizing the contractions of contralateral heart chambers using biatrial and/or biventricular pacing.

The control processor 240 may include an arrhythmia detector that operates to detect atrial or ventricular tachyarrhythmia or fibrillation. Under control of the control processor 240, the cardioversion/defibrillation pulse generator 235 is capable of generating high energy shocks to terminate the detected tachyarrhythmia episodes.

The pacing pulses and/or defibrillation shocks are delivered via multiple cardiac electrodes 205 electrically coupled to a heart and disposed at multiple locations within, on, or about the heart. One or more electrodes 205 may be disposed in, on, or about a heart chamber or at multiple sites of the heart chamber. The electrodes 205 are coupled to switch matrix 225 circuitry that is used to selectively couple the electrodes 205 to the sense circuitry 210 and the therapy pulse generators 230, 235.

The CRM system 200 includes a pacing response classification (PRC) processor 215. In some embodiments, the PRC processor 215 is configured to discriminate between capture and non-capture. In some embodiments, the PRC processor is configured to discriminate between capture, noncapture and fusion in accordance with embodiments described herein. Pacing response classification is implemented by the PRC processor 215 for capture threshold testing and/or capture verification during therapeutic pacing. The PRC processor 215 is configured to determine various thresholds and intervals useful in the analysis of signals to determine the pacing response. For example, the PRC processor 215 may determine one or more of a pacing threshold interval (PTI), a pacing artifact threshold (PAT), and/or a capture detection threshold (CDT). Discrimination between capture, noncapture, and fusion is performed by the PRC processor 215 based on comparison of a cardiac signal sensed following a pacing pulse to one or more of the intervals or thresholds.

The control processor 240 includes a capture threshold module 243 that controls the operation of capture threshold testing. The control processor 240 includes an atrial refractory period timer 241 for timing atrial refractory (ARP) and/or post ventricular atrial refractory period (PVARP) intervals following atrial and/or ventricular paces and/or senses. The control processor 200 may optionally include a retrograde management module 242 configured to control pacing during retrograde management pacing cycles. The control processor 240 may optionally include PMT management module 244 configured to control pacing during PMT management pacing cycles.

The capture threshold module 243 controls the delivery of paces by the pacing therapy pulse generator 230 during therapeutic pacing and during capture threshold testing. To determine the capture threshold, the capture threshold module 243 may control the delivery of a sequence of pacing pulses that incrementally step down or step up the pacing energy until a capture threshold is determined. Prior to beginning the capture threshold test, the capture threshold module 243 may control pacing during an initialization procedure. During the initialization procedure, the PRC processor 215 operates to determine thresholds and intervals described herein that are useful in cardiac pacing response classification. The thresholds and intervals determined in the initiation procedure are then used to determine the pacing responses to the threshold test paces.

The CRM system 200 is typically powered by an electrochemical battery (not shown). A memory 245 stores data and program commands used to implement the pacing response classification, retrograde management and/or PMT management approaches described herein along with other features. Data and program commands may be transferred between the CRM system 200 and a patient-external device 255 via telemetry-based communications circuitry 250.

Figure 2:
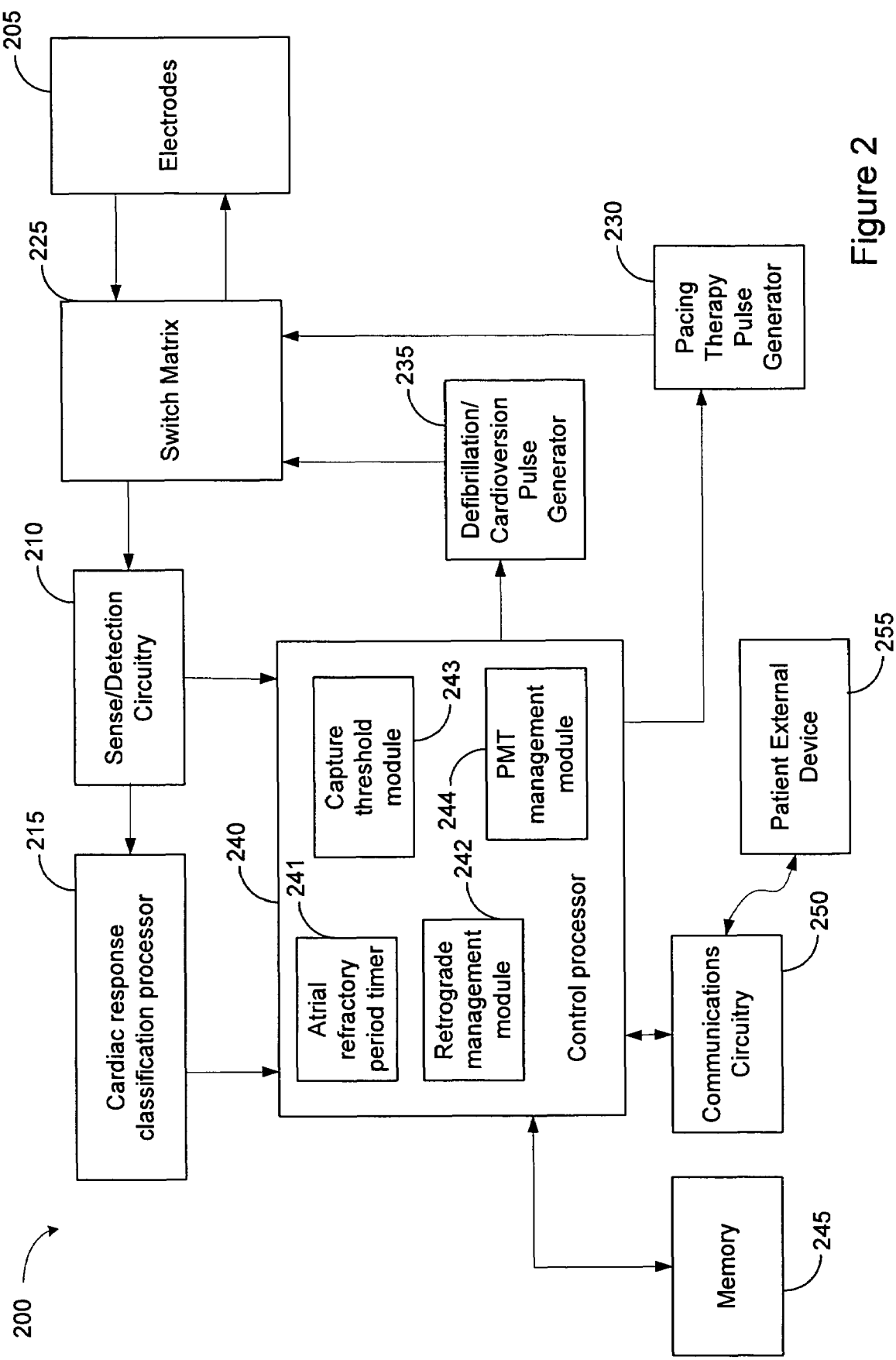
FIG. 2 is a block diagram of a pacemaker that may be used to detect atrial capture and manage atrial retrograde conduction and PMT in accordance with embodiments of the invention.

FIG. 2 shows a CRM system 200 divided into functional blocks. It is understood by those skilled in the art that there exist many possible configurations in which these functional blocks can be arranged. The example depicted in FIG. 2 is one possible functional arrangement. Other arrangements are also possible. For example, more, fewer or different functional blocks may be used to describe a cardiac system suitable for implementing the processes of the present invention. In addition, although the CRM system 200 depicted in FIG. 2 contemplates the use of a programmable microprocessor-based logic circuit, other circuit implementations may be utilized.

Figure 3:
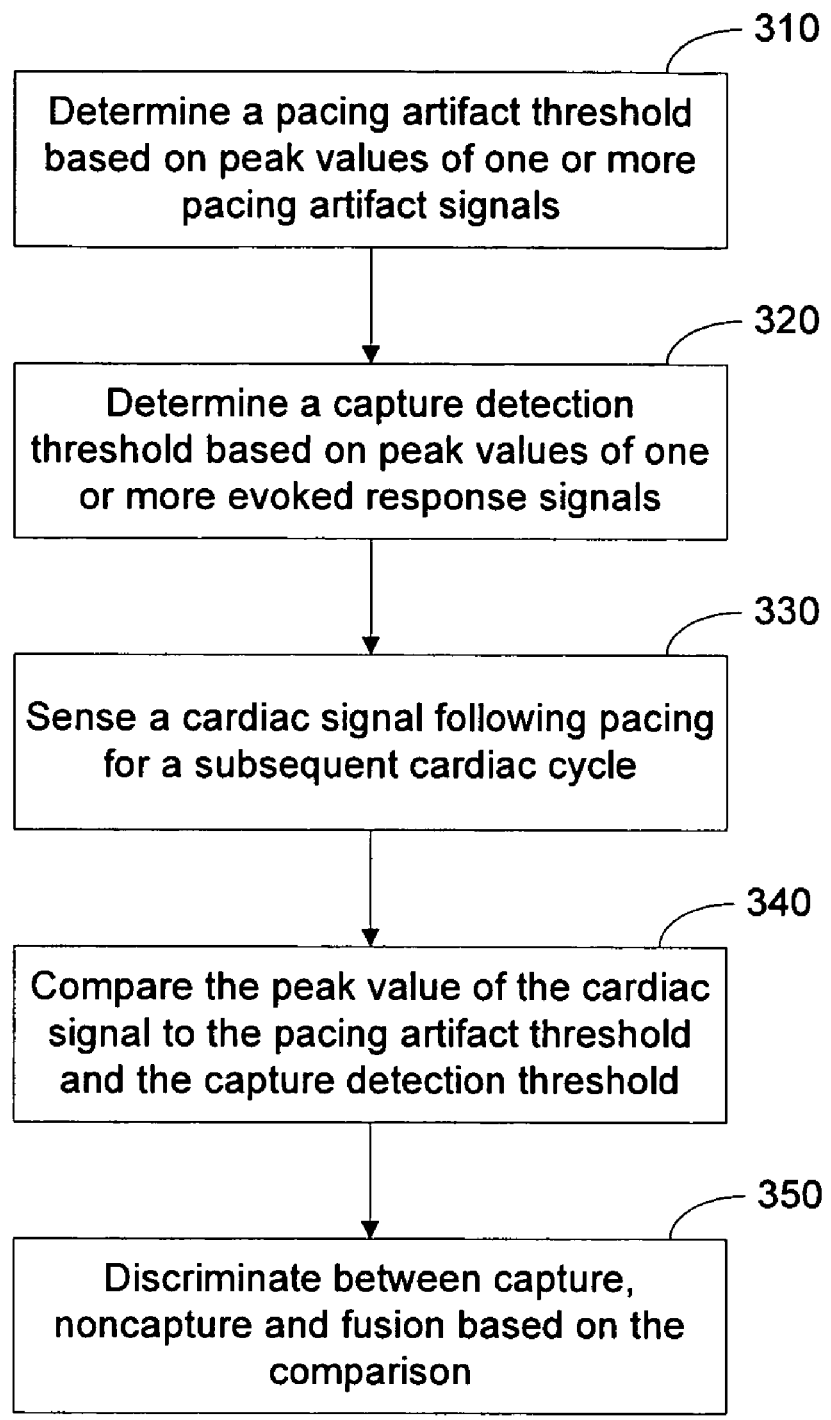
FIG. 3 is a flowchart illustrating a method for classifying the cardiac response to pacing that may be implemented by a CRM device in accordance with embodiments of the invention.

FIG. 3 is a flowchart illustrating a method for classifying the cardiac response to pacing a heart chamber, such as an atrial heart chamber, that may be implemented by a CRM device in accordance with embodiments of the invention. The time between a delivered atrial pace and the evoked response signal peak is substantially consistent. A peak timing interval (PTI) may be established for examining the cardiac signal to determine the pacing response. The magnitude of the peak may be used to classify the pacing response.

A method in accordance with one embodiment involves discriminating between capture, noncapture, and fusion based on comparison of a sensed cardiac signal peak to a capture detection threshold (CDT), a pacing artifact threshold (PAT), and a peak timing interval (PTI). The PAT is determined 310 based on peak values of atrial signals of one or more noncaptured cardiac cycles, e.g., about 2 to about 4 cardiac cycles. The signals used to determine the PAT may be sensed following sub-capture threshold paces following a capture threshold test, for example. The sensed atrial signals associated with noncapture are pacing artifact signals that have a morphology exhibiting a pacing artifact without the evoked response morphology produced by capture. In various implementations, the PAT may be based on or a combination of the peak values of the signals associated with noncapture. For example, the PAT may be based on the peak magnitude of a most recent cardiac signal associated with capture, the largest one or more peak magnitudes of the signals associated with noncapture, a median value of the magnitudes of the signals associated with noncapture, a mean value of the magnitudes of the signals associated with noncapture, a weighted average of the magnitudes of the signals associated with noncapture, or other combination of the peak magnitudes of the signals associated with noncapture. The PAT may include an offset to take into account the variability of the peak magnitudes of the signals associated with noncapture. In one example, the PAT is set to a percentage, such as about 150%, of the peak magnitude of a most recent signal associated with noncapture.

A capture detection threshold (CDT) is determined 320 based on peak values of one or more evoked response signals, e.g., about 5 to about 10 signals, detected during one or more captured cardiac cycles. The signals used to determine the CDT follow supra capture threshold paces. The signals associated with capture exhibit a morphology that includes an evoked response signal having a superimposed pacing artifact signal. Similarly to the PAT determination described above, the CDT may be based on or a combination of the peak values of the signals associated with capture. The CDT may be based on a most recent peak magnitude of a signal associated with capture, the largest one or more peak magnitudes of the signals associated with capture, a median value of the peak magnitudes of the signals associated with capture, a mean value of the peak magnitudes of the signals associated with capture, or a weighted average of the peak magnitudes of the signals associated with capture, or other combination of the peak magnitudes of the signals associated with capture. The CDT may include an offset to take into account the variability of the peak magnitudes of the signals associated with capture. The use of a weighted average for the CDT provides such an offset, for example. In one embodiment, the CDT is set to a percentage of an average, e.g., about 70% of evoked response peak magnitudes.

A peak time interval (PTI) associated with an expected timing of the evoked response signal peak is used in conjunction with the PAT and the CDT. Discrimination between capture, noncapture, and fusion is based on comparison of the magnitude of the cardiac signal peak relative to the PAT and CDT and comparison of the timing of the cardiac signal peak relative to the PTI.

The PTI is determined based on the timing of peak values of one or more evoked response signals detected during one or more captured cardiac cycles. The signals used to determine the PTI follow supra capture threshold paces. The PTI may be determined based on the variability of the peak timing of the signals associated with capture, for example. A typical value of the PTI is about 9 ms, for example. The PTI may be based on a median value of the peak timings of the signals associated with capture, a mean value of the peak timings of the signals associated with capture, or a weighted average of the peak timings of the signals associated with capture, or other combination of the peak timings of the signals associated with capture. The PTI may include predetermined interval offsets on either side of a most recent, average, mean, or median timing value, for example, where the interval offsets take into account the variability of the peak timing of signals associated with capture.

A cardiac signal following a pacing pulse of a cardiac cycle subsequent to the noncaptured cardiac cycles and the captured cardiac cycles is sensed 330. A peak value of the sensed cardiac signal falling within the PTI is compared 340 to the PAT and to the CDT. The device discriminates 350 between capture, noncapture, and fusion based on the comparison. If the signal peak is less than the PAT, then the pacing response is determined to be noncapture. If the signal peak is greater than the CDT, then the pacing response is determined to be capture. If the signal peak falls between the PAT and the CDT, then the pacing response may be noncapture or may be fusion.

Figure 4A:
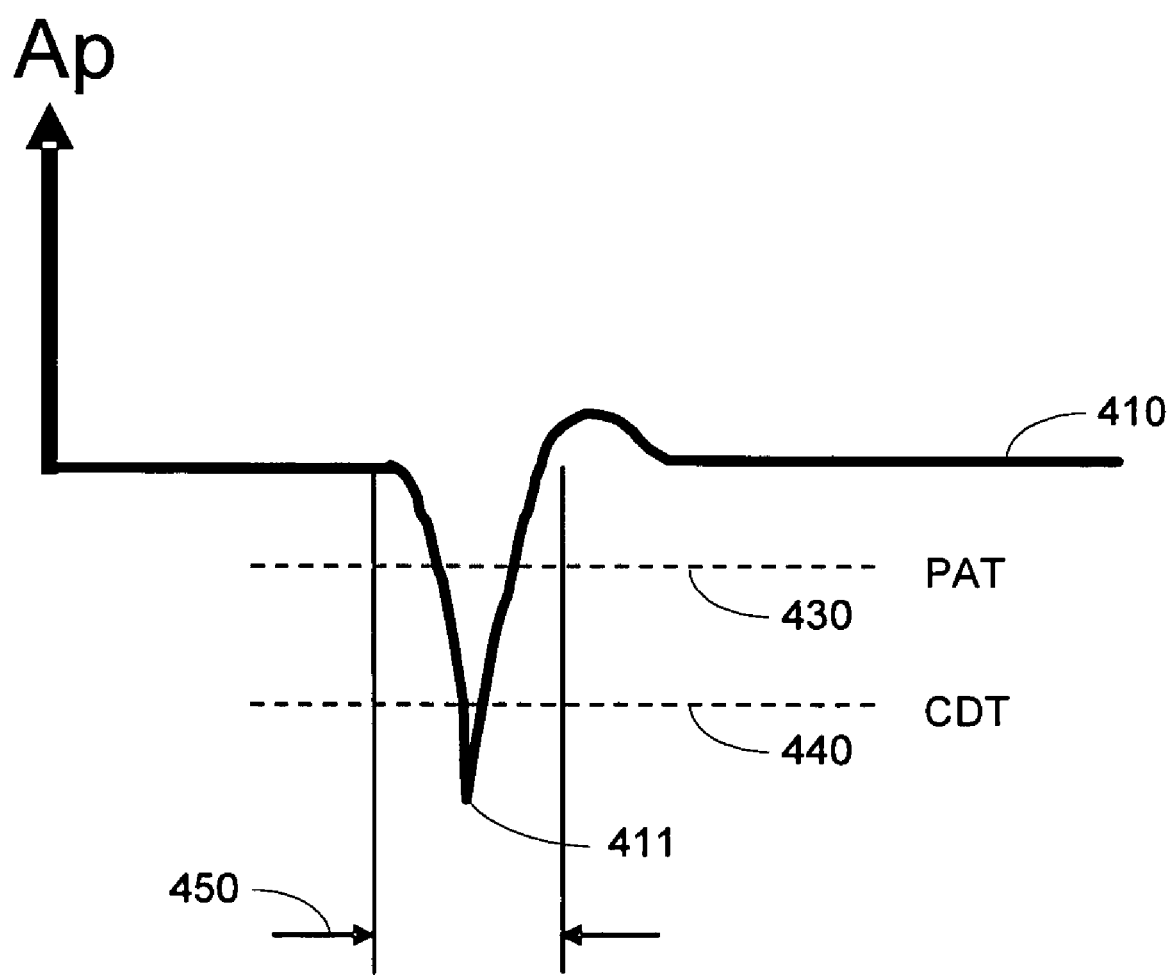
FIG. 4A is a graph illustrating the morphology of a cardiac signal sensed following an atrial pace.

FIG. 4A is a graph illustrating the morphology of a captured response signal 410 sensed following an atrial pace (Ap). The peak 411 of the cardiac signal 410 depicted in FIG. 4A has a magnitude (i.e., absolute value) larger than the PAT 430 and the CDT 440.

Figure 4B:
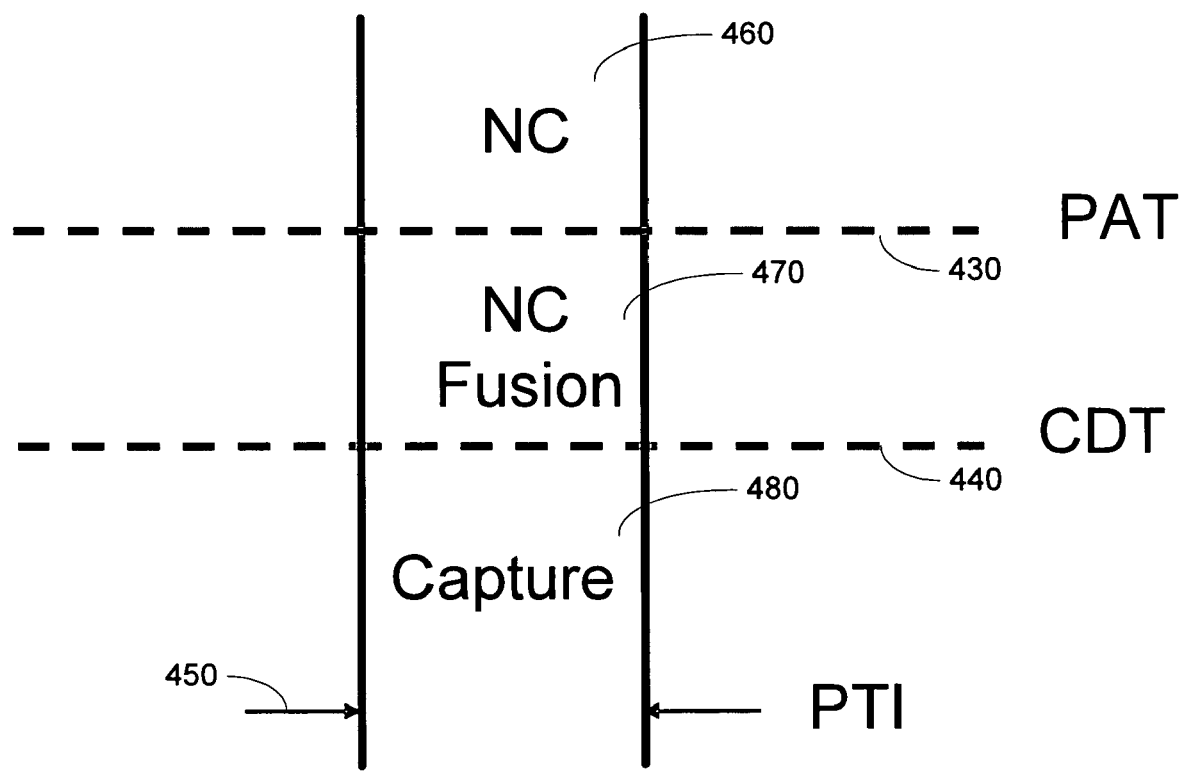
FIG. 4B is a diagram illustrating regions within the peak timing interval used in pacing response discrimination in accordance with embodiments of the invention.

FIG. 4B is a diagram illustrating regions used in pacing response discrimination in accordance with one embodiment. FIG. 4B shows the PAT 430, the CDT 440, and the PTI 450 which define regions 460, 470, and 480 respectively associated with noncapture (NC), capture, and both noncapture and fusion. If the peak of a cardiac signal following pacing falls within a particular region 460, 470, 480, then the cardiac pacing response is classified as likely to be the type of response or responses associated with the region 460, 470, 480.

In one implementation, a counter for a particular type of response is incremented each time a peak falls within a region associated with the particular type of response. The counter increments may be integer or fractional increments. The counter increments may be based on the likelihood that a particular type of pacing response has occurred. For example, region 470 is associated with both noncapture and fusion. However, it may be more likely that a peak falling in region 470 is fusion rather than noncapture. If a peak falls within region 470, the fusion counter may be incremented by 1 and the noncapture counter may be incremented by ½. In some scenarios, confirmation that a particular pacing response has been occurring may require several cardiac cycles. For example, confirmation of the particular type of pacing response may occur if a counter for the particular type of pacing response reaches a predetermined value.

Figure 5:
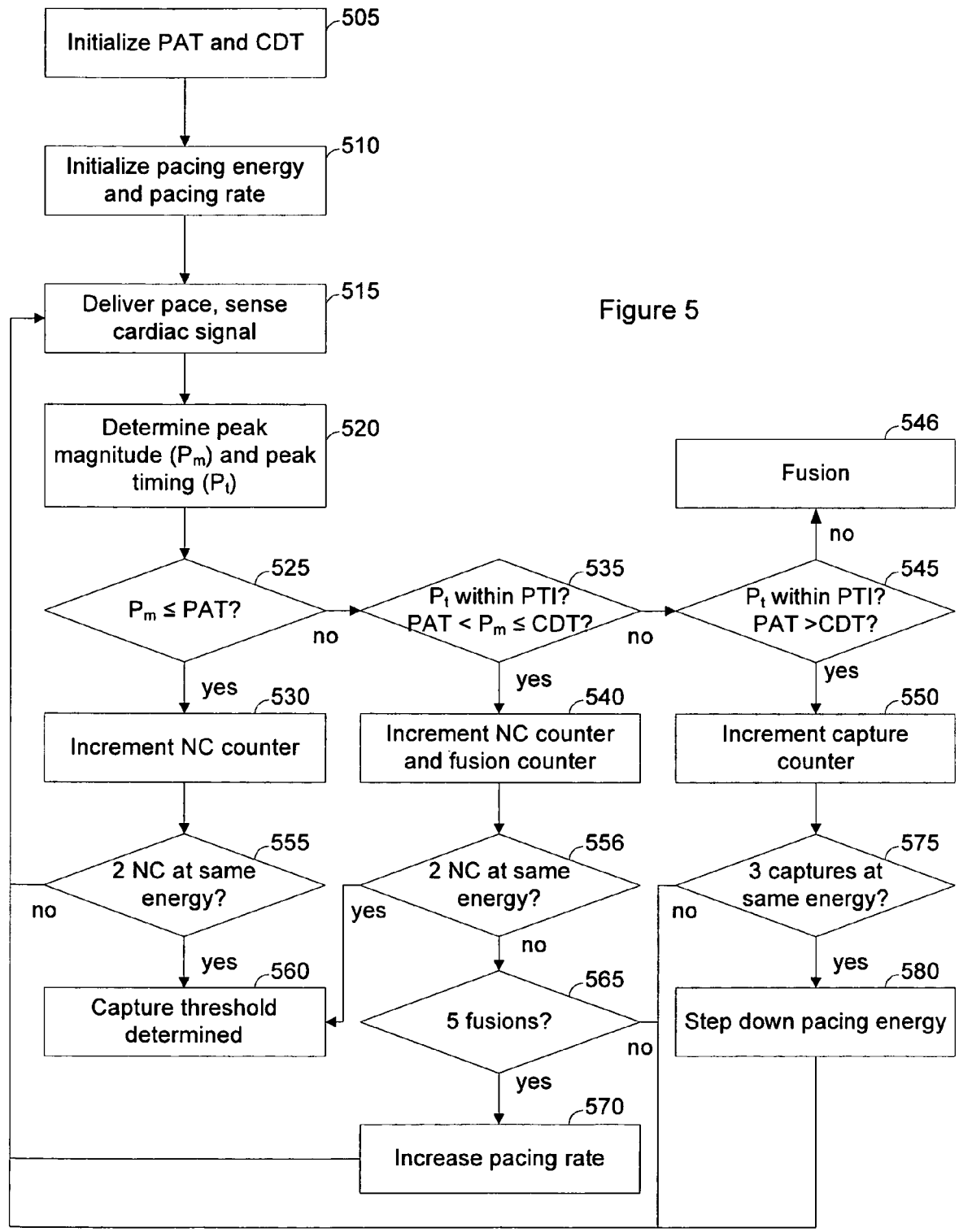
FIG. 5 is a flowchart illustrating step down capture threshold testing with pacing response classification based on the regions depicted in FIG. 4B in accordance with embodiments of the invention.

FIG. 5 is a flowchart illustrating step down capture threshold testing with pacing response classification based on the regions depicted in FIG. 4B. The approaches of the present invention may advantageously be used in connection with capture threshold testing. Prior to beginning the step down test, the CDT and/or PTI are initialized 505 based on the peak magnitudes of signals sensed following delivery of a series of supra capture threshold paces.

In one embodiment, the PAT is initialized to a predetermined value, such as about 0.3 mV prior to the capture threshold test. The CDT and PTI are initialized based on measured values of the peak magnitude and peak timing of captured signals Initialization of the CDT and PTI prior to the test based on measured values provides patient specific values, enhancing the accuracy of capture testing. In addition, one or more of these parameters may be modified during and/or after the capture threshold test based on most recent peak timing and peak magnitude values to further enhance the test accuracy.

The pacing energy and the pacing rate are initialized 510 for the test. A pace is delivered 515 and the cardiac signal following the pace is sensed 515. The peak magnitude ($P_M$) of the cardiac signal is determined 520. If the peak magnitude is less than or equal to 525 the PAT, then the pace did not capture the chamber and the noncapture counter is incremented 530. If the peak timing is within the PTI and the peak magnitude is greater than the PAT but is less than or equal to the CDT 535, then the pacing response may be noncapture or may be fusion. Both the noncapture counter and the fusion counter are incremented 540. If the peak timing is within the PTI and the peak magnitude is greater than the CDT, then the pacing response is 545 capture and the capture counter is incremented 550. Otherwise, the response is determined 546 to be fusion.

The amounts that the counters for each type of response are incremented may be integer or fractional amounts. In some implementations, the amount that a particular counter is incremented is associated with the likelihood that the type of pacing response occurred. For example, if the peak magnitude falls between the PAT and the CDT, fusion is more likely than noncapture. In this scenario, the fusion counter may be incremented by 1 and the noncapture counter incremented by ½.

If the noncapture counter reaches 555, 556 a predetermined value, e.g., about 2, for paces having the same energy, then loss of capture is confirmed and the capture threshold is determined 560. If the fusion counter reaches a predetermined value, e.g., about 5, then the pacing rate is increased 570 to decrease the occurrence of fusion beats. If the capture counter reaches 575 a predetermined value, e.g., about 3 for paces having the same energy, then the pacing energy is stepped down 580 and the test continues until the capture threshold is determined 560.

In some implementations, the PAT, CDT, and PTI may be initialized before the test and/or one or more of these parameters may be modified during the test, such as during every cardiac cycle, and/or may be modified after the test. The PAT may be re-initialized in the case of certain failures.

In one example, the peak timing and/or peak magnitude may be determined for the cardiac signal of each beat. The peak timing and/or peak magnitude may be combined with peak timings and magnitudes of one or more previous beats to dynamically modify the PTI and CDT during the test. Modifying the PTI and/or CDT during the test may be used to adapt to changing patient conditions, providing more accurate values for these parameters. The PAT may be modified after the test based on one or more noncaptured signals, detected after the capture threshold is determined. Modifying the PAT based on a particular patient's pacing artifact morphology allows for adaptation to changing patient conditions over time and provides more accurate pacing response classification.

Figure 6:
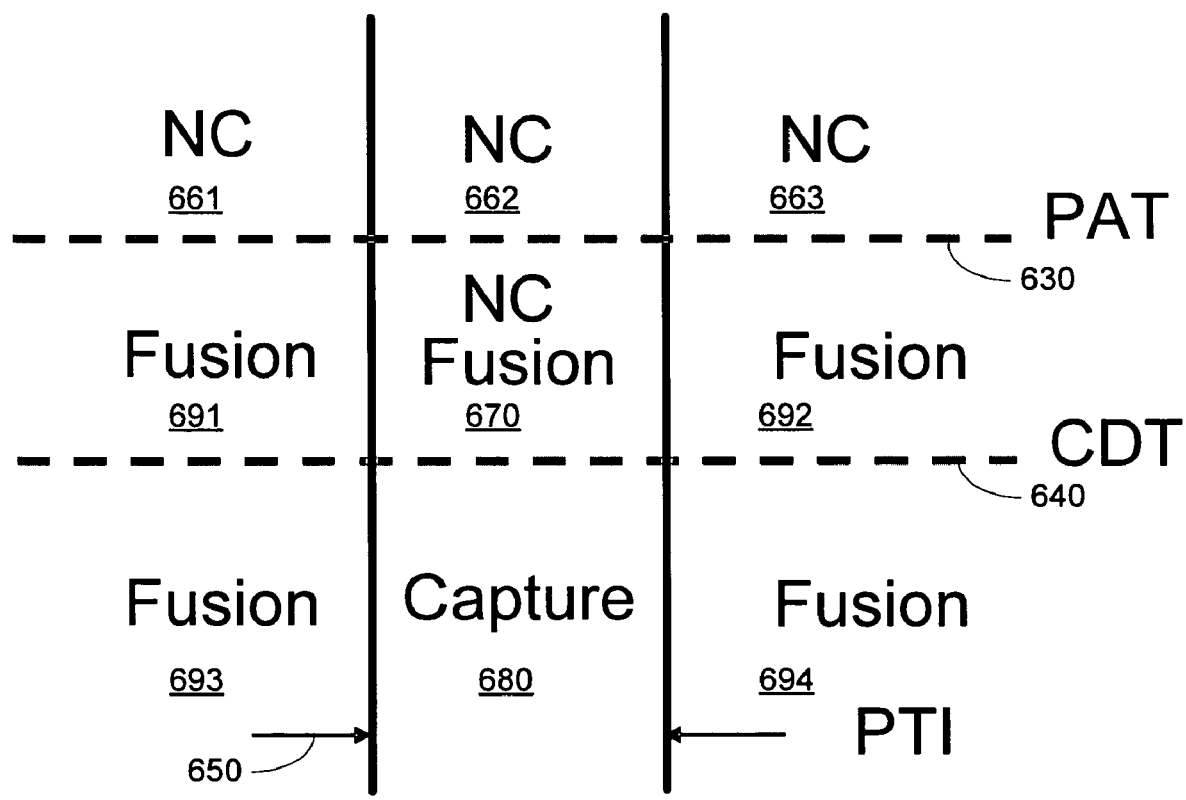
FIG. 6 is a diagram illustrating regions used in pacing response discrimination in accordance with embodiments of the invention.

FIG. 6 is a diagram illustrating regions used in pacing response discrimination in accordance with another embodiment. Fusion beats usually exhibit large variations in peak timing of the cardiac signal when compared to captured beats. Regions corresponding to time intervals before and/or after the PTI may be used for fusion discrimination. FIG. 6 shows the PAT 630, the CDT 640, and the PTI 650 which define regions 661-663 associated with noncapture, region 670 associated with noncapture and fusion, region 680 associated with capture, and regions 691-694 associated with fusion. If the peak of a cardiac signal following pacing falls within a particular region, then the cardiac pacing response is likely to be the type of response associated with the region.

As previously described, a counter for a particular type of response may be incremented each time a peak falls within a region associated with the particular type of response. The increments may be integer or fractional increments. The counter increments may be based on the likelihood that a particular type of pacing response has occurred. For example, region 670 is associated with both noncapture and fusion. However, it may be more likely that a peak falling in region 670 is fusion rather than noncapture. If a peak falls within region 670, the fusion counter may be incremented by 1 and the noncapture may be incremented by ½. In some scenarios, confirmation that a particular pacing response has been occurring may require several cardiac cycles. For example, confirmation of the particular type of pacing response may occur if a counter for the particular type of pacing response reaches a predetermined value.

Figure 7A:
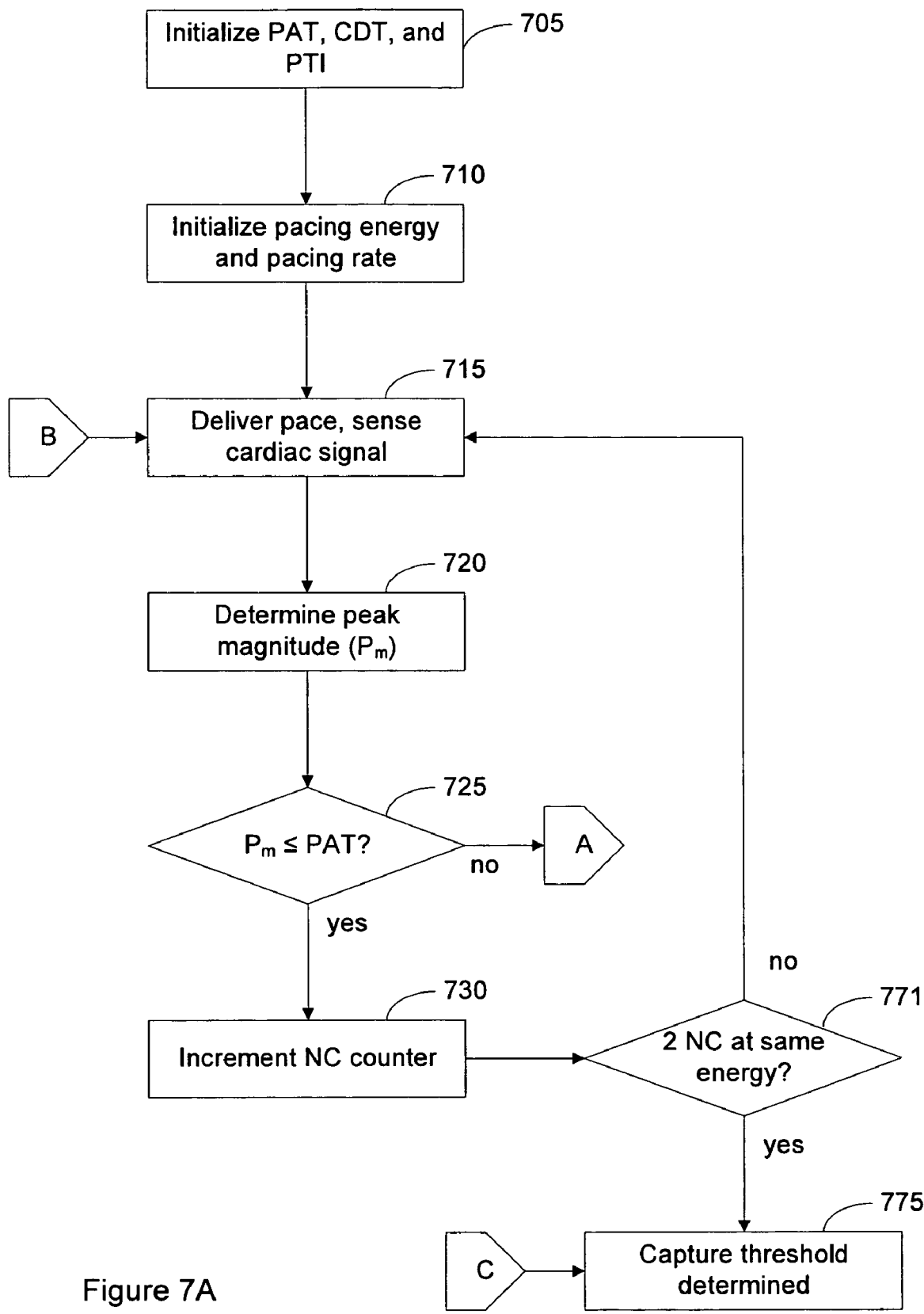
FIGS. 7A-7B illustrate a flowchart illustrating step down capture threshold testing with pacing response classification based on the regions depicted in FIG. 6 in accordance with embodiments of the invention.
Figure 7B:
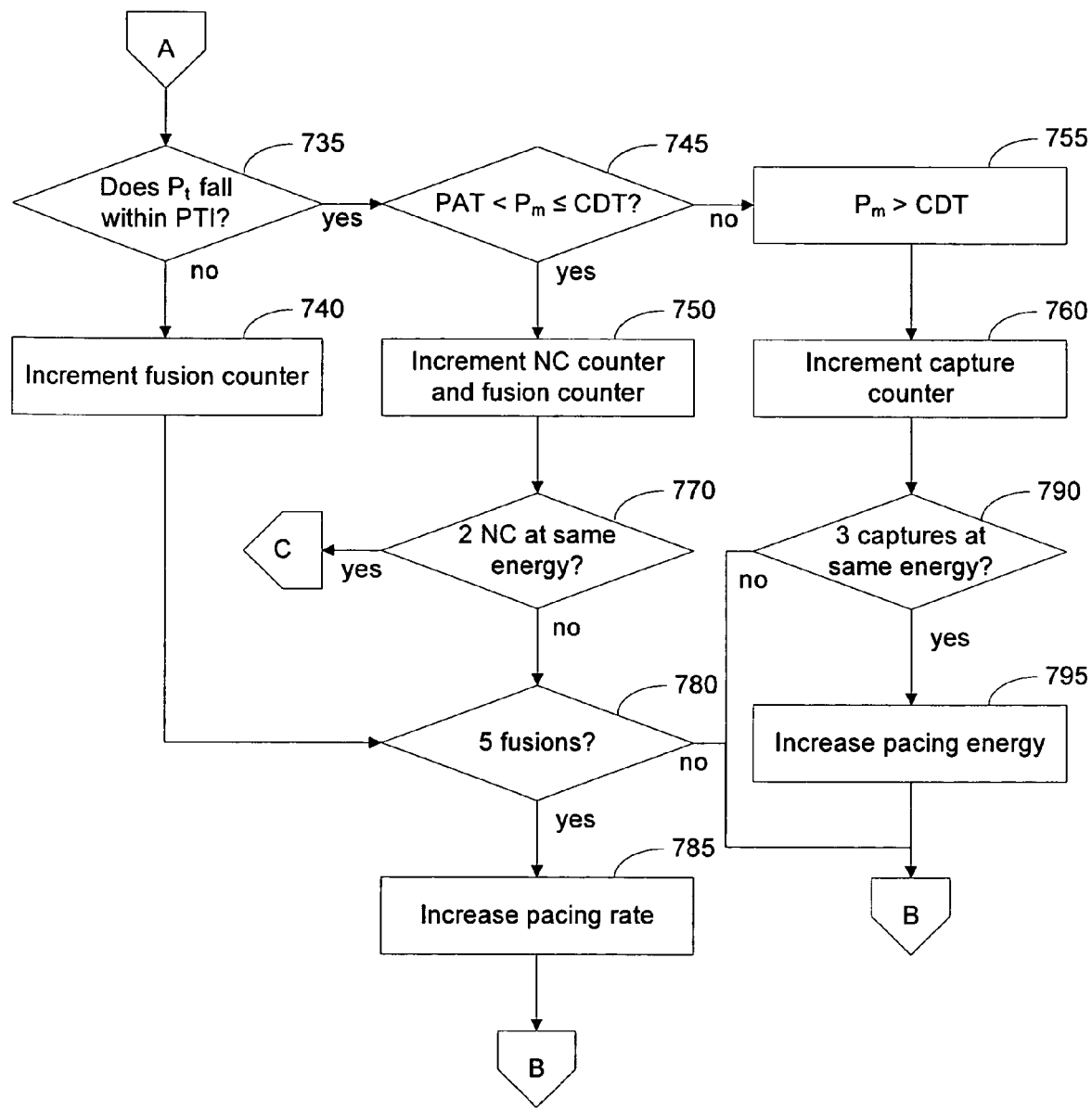

FIGS. 7A-7B illustrate a flowchart illustrating step down capture threshold testing with pacing response classification based on the regions depicted in FIG. 6. Prior to beginning the step down test, the PAT, CDT, and PTI are initialized 705. The PAT is initialized to a predetermined value. The CDT is initialized based peak magnitudes, $P_m$, of signals sensed following delivery of supra capture threshold paces. PTI is initialized based on the peak timing, $P_t$, of signals sensed following delivery of supra capture threshold paces. The pacing energy and the pacing rate are initialized 710 for the test.

A pace is delivered 715 and the cardiac signal following the pace is sensed 715. The peak magnitude, $P_m$, of the cardiac signal is determined 720. If the peak magnitude is less than or equal to 725 the PAT, then the pace did not capture the chamber and the noncapture counter is incremented 730. If the peak magnitude is greater than the PAT and the timing of the peak does not fall 735 within the PTI, then the pacing response is likely to be fusion and the fusion counter is incremented 740.

If the timing of the peak falls within the PTI and the peak magnitude is greater than the PAT and less than or equal to 745 the CDT, then the pacing response may be fusion or noncapture. The fusion counter and the noncapture counter are incremented 750. If the peak magnitude is greater than the CDT, then the pacing response is 755 capture and the capture counter is incremented 760.

As previously described, the amounts that the counters for each type of response are incremented may be integer or fractional amounts. In some implementations, the amount that a particular counter is incremented is associated with the likelihood that the type of pacing response occurred. For example, if the peak magnitude falls between the PAT and the CDT, fusion is more likely than noncapture. In this scenario, the fusion counter may be incremented by 1 and the noncapture counter incremented by ½.

If the noncapture counter reaches 770, 771 a predetermined value, e.g., about 2, for paces having the same energy, then loss of capture is confirmed and the capture threshold is determined 775. If the fusion counter reaches 780 a predetermined value, e.g., about 5, then the pacing rate is increased 785 to avoid the occurrence of fusion beats. If the capture counter reaches 790 a predetermined value, e.g., about 3 for paces having the same energy, then the pacing energy is stepped down 795 and the test continues until the capture threshold is determined 775. Following the capture threshold test, the PAT may be updated based on the peak magnitude of one or more noncaptured signals During pacing, if noncapture occurs, retrograde conduction from an intrinsic or paced ventricular depolarization may cause a false noncapture detection on the next pacing cycle. Retrograde conduction during capture threshold testing, for example, may lead to erroneous capture threshold determination. Retrograde conduction may also cause undesirable fast pacing, denoted pacemaker mediated tachyarrhythmia (PMT). Some embodiments described herein include methods and systems that provide for management of retrograde conduction and PMT.

Figure 8:
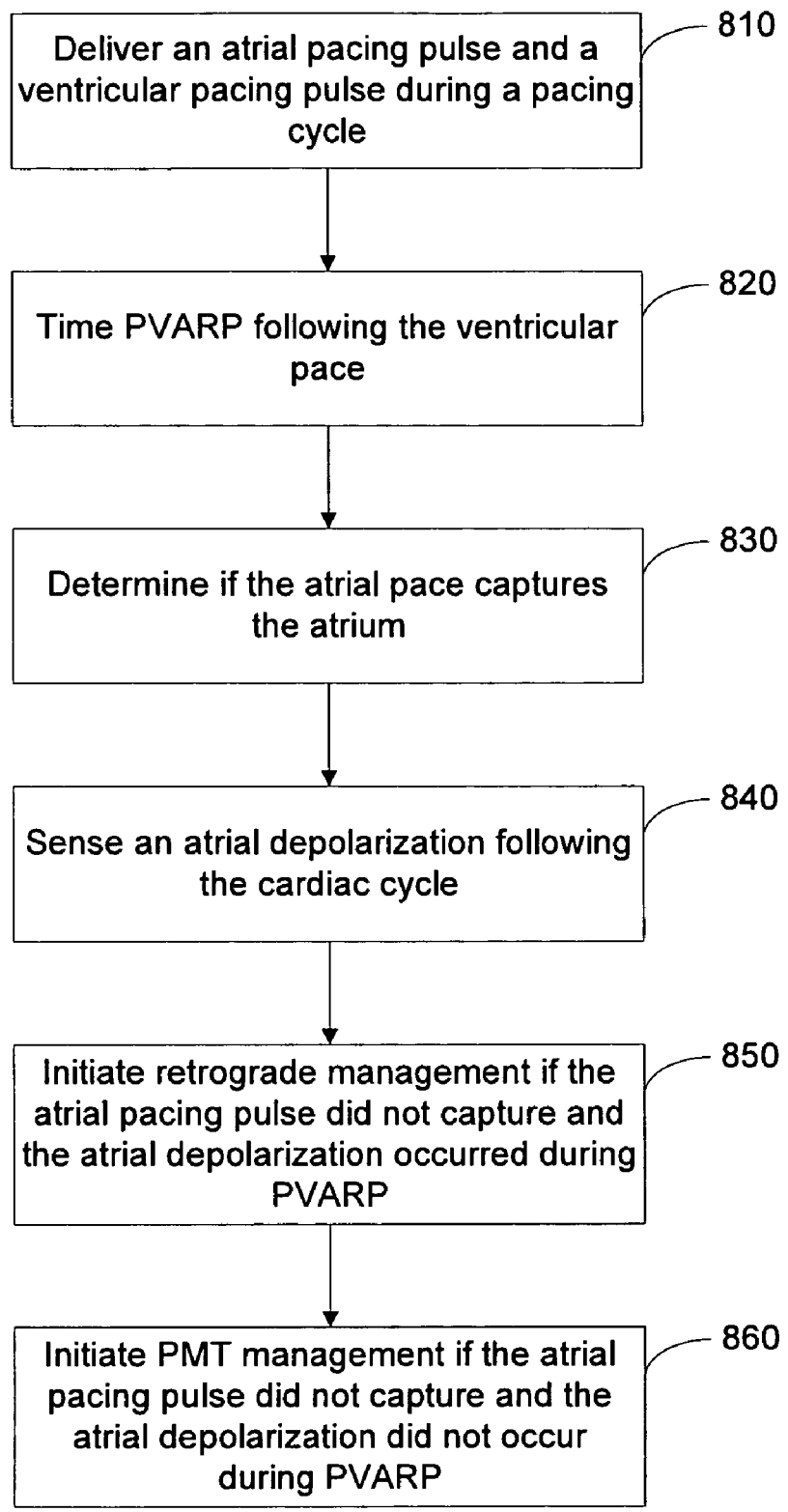
FIG. 8 is a flowchart that illustrates an approach implementable in a CRM system for retrograde conduction management and PMT management in accordance with embodiments of the invention.

The flowchart of FIG. 8 illustrates an approach implementable in a CRM system for retrograde conduction management and PMT management in accordance with embodiments of the invention. An atrial pace and a ventricular pace are delivered 810 during a cardiac cycle. A post ventricular atrial refractory period (PVARP) is timed 820 following the ventricular pace. The CRM system determines 830 if the atrial pace captured the atrium. In some embodiments, capture may be detected based on comparison of peak magnitude and timing of the cardiac signal following pacing to the CDT, PAT, and PTI as described above. In other embodiments, capture may be determined using other capture detection methods known in the art.

If capture occurs, the depolarization associated with capture causes tissue refractoriness, making retrograde conduction unlikely. If noncapture occurs, the atrial tissue is not refractory after the pace and the ventricular depolarization may conduct retrogradely to the atrium. The system senses 840 an atrial depolarization following the pacing cycle indicative of retrograde conduction. Retrograde management is initiated 850 if the atrial pacing pulse did not capture and an atrial depolarization is sensed during the PVARP. PMT management is initiated 860 if the atrial pacing pulse did not capture and an atrial depolarization is sensed after the PVARP.

Figure 9:
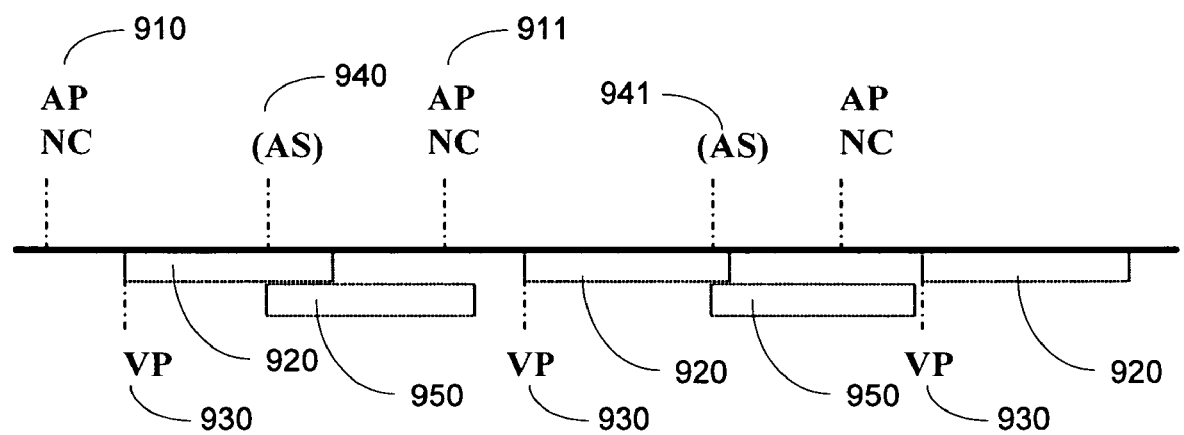
FIG. 9 is a timing diagram illustrating a scenario where loss of capture may be erroneously detected due to retrograde conduction.

The timing diagram of FIG. 9 illustrates a scenario where noncapture is erroneously detected due to retrograde conduction. A noncaptured atrial pace 910 and a ventricular pace 930 are delivered during a first cardiac cycle. A PVARP 920 is timed is following the ventricular pace 930. In this cycle, the atrial pace may be accurately detected as noncapture. However, confirmation of the loss of capture during a capture threshold test typically requires more than one noncaptured pace, such as several noncaptured paces detected consecutively or within a short period of time. If a noncapture event was caused by transient effects, such as noise, rather than by the decrease in the pacing energy, then loss of capture would not be confirmed because subsequent paces would be captured and the test would continue. However, a pattern of retrograde conduction may be initiated by the noncaptured pace, causing a single noncaptured pace to result in an erroneous loss of capture confirmation as described below.

Because the atrial pace 910 did not produce capture, the depolarization caused by the ventricular pace causes retrograde conduction to the atrium. The retrograde conduction produces an atrial depolarization 940 causing the atrial tissue to become refractory. The atrial depolarization 940 does not initiate a new pacing cycle because is occurs during PVARP 920. The atrial pace 911 for the next cycle is delivered during the tissue refractory period 950. Because the atrial pace 911 is delivered while the tissue is refractory, the pace 911 is detected as noncapture. During a capture threshold test, the noncaptured atrial pace causes a false detection of noncapture because the noncapture is the result of tissue refractoriness following retrograde conduction rather than the change in the pacing energy level. Noncapture of the atrial pace 911 during the second cardiac cycle again causes retrograde conduction, an atrial depolarization 941, and tissue refractoriness. The pattern of false noncapture detection and retrograde conduction may continue resulting in a confirmation of loss of capture and an erroneous capture threshold measurement.

Figure 10:
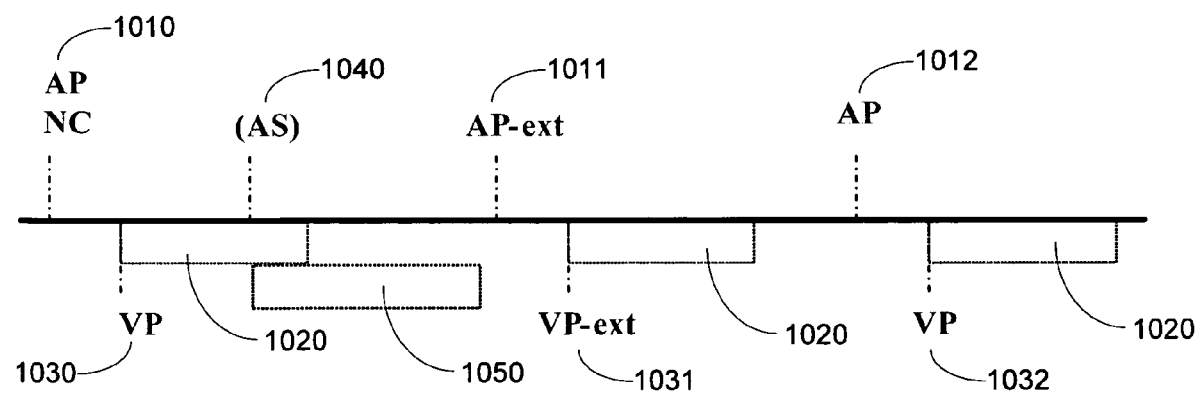
FIG. 10 is a timing diagram illustrating retrograde management in accordance with embodiments of the invention.

The timing diagram illustrated in FIG. 10 illustrates retrograde management in accordance with embodiments of the invention. The atrial pace 1010 of the first cardiac cycle is noncaptured. The ventricular pace 1020 of the first cardiac cycle causes retrograde conduction to the atrium. An atrial depolarization 1040 produced by the retrograde conduction causes the atrial tissue to become refractory during a tissue refractory period 1050. The atrial depolarization 1040 does not initiate a new pacing cycle because the atrial depolarization occurs during PVARP 1020. The CRM system senses the atrial depolarization 1040 that occurs during the PVARP 1020. The next scheduled atrial pace 1011 for the cycle following the retrograde conduction is delayed until after the tissue refractory period 1050 ends. Typically the period 1050 of tissue refractoriness lasts less than 300 ms after the depolarization 1040 is sensed, for example. Therefore, the next scheduled atrial pace 1011 in this example is delayed until about 300 ms following the atrial depolarization 1040.

The delayed pace 1011 is correctly classified as a captured pace. The third cardiac cycle includes an atrial pace 1012 and a ventricular pace 1032 that are delivered at the scheduled time.

Figure 11:
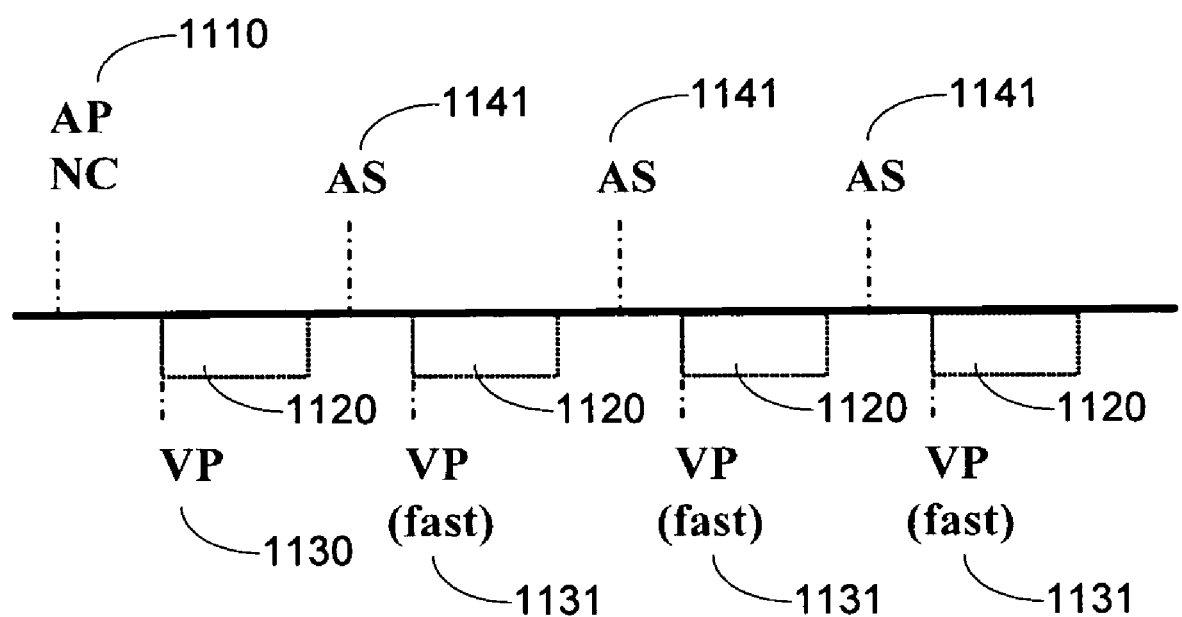
FIG. 11 is a timing diagram illustrating PMT caused by retrograde conduction.

FIGS. 9 and 10 above illustrate retrograde conduction when the retrograde atrial depolarization occurs during PVARP. In this scenario, the retrograde atrial depolarization does not initiate a new pacing cycle. Retrograde conduction producing atrial depolarizations that occur after PVARP has expired may result in PMT. PMT caused by retrograde conduction is illustrated in the timing diagram of FIG. 11. The first cardiac cycle includes a noncaptured atrial pace 1110 and a captured ventricular pace 1130. PVARP 1120 is timed following the ventricular pace 1130, 1131 for each cycle. The noncaptured atrial pace 1110 in the first cycle allows the depolarization initiated by the captured ventricular pace 1130 of the first cycle to conduct retrogradely to the atrium. An atrial depolarization caused by the retrograde conduction causes a nonrefractory atrial sense. Because the atrial sense 1141 occurs after expiration of PVARP 1120 (i.e., is a nonrefractory sense), the CRM system initiates a pacing cycle in the second cardiac cycle which is abnormally fast. The pattern of fast ventricular paces and retrograde atrial depolarizations that occur after PVARP continues in the third and fourth cycles. The pacing cycles of FIG. 11 illustrate PMT.

Figure 12:
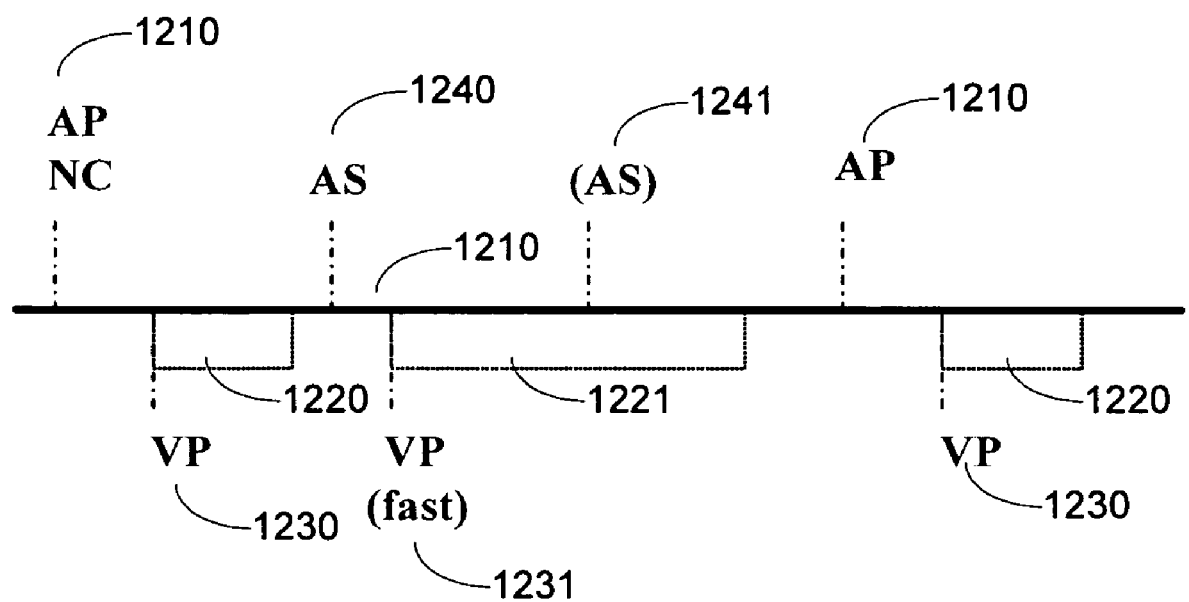
FIG. 12 is a timing diagram illustrating PMT management in accordance with embodiments of the invention.

The timing diagram illustrated in FIG. 12 illustrates PMT management in accordance with embodiments of the invention. The first pacing cycle includes a noncaptured atrial pace 1210 and a captured ventricular pace 1230. The noncaptured atrial pace 1210 allows the depolarization caused by the ventricular pace to be retrogradely conducted to the atrium. The retrograde conduction occurs after PVARP for the cycle has expired. The nonrefractory atrial sense 1240 caused by the retrograde conduction is used by the CRM system to initiate a pacing cycle. The next ventricular pace 1231 is fast.

The CRM system initiates PMT management following the noncaptured atrial pace 1210 in the first cycle and the nonrefractory atrial sense 1240 initiating the second cycle. The PVARP 1221 for the pacing cycle following the noncaptured pace 1210, which is the second cycle illustrated in FIG. 12, is extended to break the PMT pattern. The next atrial sense 1241 occurs in the extended PVARP 1221 and does not initiate a pacing cycle. The third cardiac cycle illustrated in FIG. 12 is a normal cycle.

Figure 13:
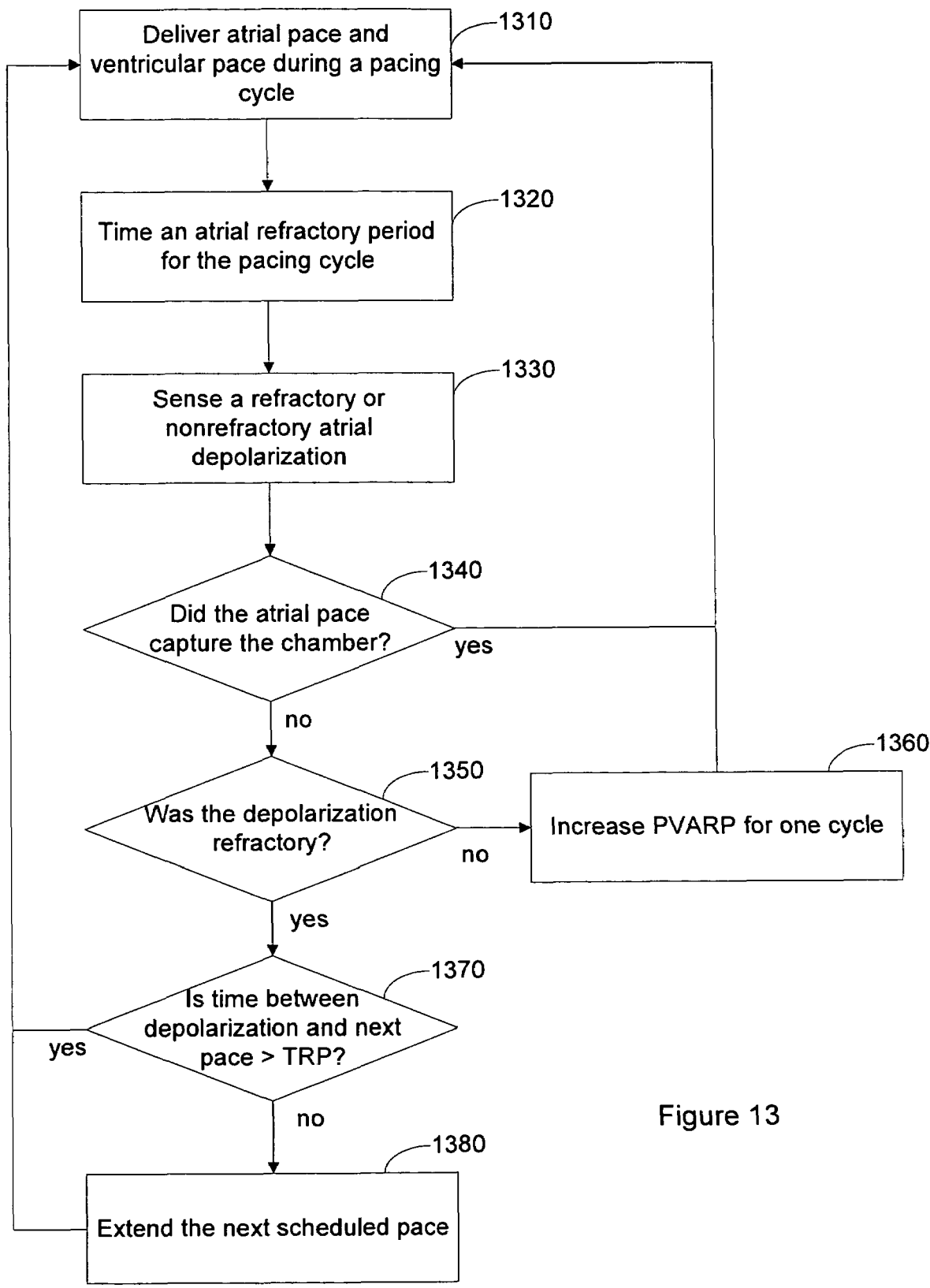
FIG. 13 is a flowchart illustrating retrograde management and PMT management in accordance with embodiments of the invention.

The flowchart of FIG. 13 illustrates retrograde conduction management and PMT management in accordance with embodiments of the invention. An atrial and ventricular pace are delivered 1310 during a pacing cycle. An atrial refractory period is timed 1320 for the pacing cycle. A refractory or nonrefractory atrial depolarization is sensed 1330. If the atrial pace did not capture 1340 the atrium and the atrial depolarization was sensed 1350 after expiration of the refractory period, then PVARP is increased 1360 for one cardiac cycle. For example, the PVARP may be extended to about 500 ms. Extending the PVARP to 500 ms for one cardiac cycle breaks the PMT.

If the atrial pace did not capture 1340 the atrium and the atrial depolarization was sensed 1350 during the refractory period, the system checks to determine 1370 if the time between the atrial depolarization and the next scheduled atrial pace is greater than the tissue refractory period (TRP). If not, the time for the next scheduled pace is extended 1380 to avoid retrograde conduction in subsequent cardiac cycles. For example, the time for the next pace may be extended so that there is about 300 ms between the refractory atrial sense and the next pace.

A number of the examples presented herein involve block diagrams illustrating functional blocks used for coordinated monitoring, diagnosis and/or therapy functions in accordance with embodiments of the present invention. It will be understood by those skilled in the art that there exist many possible configurations in which these functional blocks can be arranged and implemented. The examples depicted herein provide examples of possible functional arrangements used to implement the approaches of the invention.

It is understood that the components and functionality depicted in the figures and described herein can be implemented in hardware, software, or a combination of hardware and software. It is further understood that the components and functionality depicted as separate or discrete blocks/elements in the figures in general can be implemented in combination with other components and functionality, and that the depiction of such components and functionality in individual or integral form is for purposes of clarity of explanation, and not of limitation.

Various modifications and additions can be made to the preferred embodiments discussed hereinabove without departing from the scope of the present invention. Accordingly, the scope of the present invention should not be limited by the particular embodiments described above, but should be defined only by the claims set forth below and equivalents thereof.

What is claimed is:

1. A method, comprising:
   delivering an atrial pacing pulse and a ventricular pacing pulse during a first paced cardiac cycle;
   timing a post ventricular atrial refractory period (PVARP) following the ventricular pacing pulse;
   determining if the atrial pacing pulse captures the atrium;
   scheduling delivery of a second atrial pacing pulse in a second cardiac cycle that occurs next after the first paced cardiac cycle; and
   in response to a determination that the atrial pacing pulse did not capture the atrium:
   sensing an atrial depolarization occurring after delivery of the first paced cardiac cycle;
   determining whether the atrial depolarization occurs during or after the PVARP;
   in response to a determination that the atrial depolarization occurred during the PVARP, initiating retrograde management, to avoid retrograde conduction in subsequent cardiac cycles, by delaying a next scheduled atrial pacing pulse if the next scheduled atrial pacing pulse is scheduled to occur when the atrial tissue is refractory; and
   in response to a determination that the atrial depolarization occurred after the PVARP, initiating pacemaker mediated tachyarrhythmia (PMT) management, to avoid PMT in subsequent cardiac cycles, by extending a subsequent PVARP of the second cardiac cycle.

2. The method of claim 1, wherein initiating the retrograde management comprises modifying pacing for at least one pacing cycle.

3. The method of claim 1, wherein delaying the next scheduled atrial pacing pulse comprises delaying the next scheduled atrial pacing pulse until about 300 ms from the atrial depolarization.

4. The method of claim 1, wherein extending the subsequent PVARP comprises extending the subsequent PVARP to about 500 ms.

5. The method of claim 1, wherein the atrial depolarization comprises a retrogradely conducted depolarization responsive to the ventricular pacing pulse.

6. The method of claim 1, wherein the atrial depolarization comprises a premature atrial contraction.

7. A cardiac rhythm management system, comprising:
- a pulse generator configured to deliver an atrial pacing pulse and a ventricular pacing pulse via electrodes coupled to a heart during a first paced cardiac cycle;
- a post ventricular atrial refractory period (PVARP) timer configured to time a PVARP following the ventricular pacing pulse;
- a capture detector configured to determine if the atrial pacing pulse captures the atrium;
- a sensing system;
- a controller coupled to the capture detector and the sensing system, the controller configured to:
  - (a) in response to a determination that the atrial pacing pulse captured the atrium, schedule delivery of a second atrial pacing pulse in a second cardiac cycle that occurs next after the first paced cardiac cycle; and
  - (b) in response to a determination that the atrial pacing pulse did not capture the atrium, use the sensing system to sense an atrial depolarization occurring after delivery of the atrial and ventricular pacing pulses, and determine whether such atrial depolarization occurs during or after the PVARP, whereupon:
    - in response to a determination that the atrial depolarization occurred during the PVARP, using a retrograde management module to initiate retrograde management pacing, to avoid retrograde conduction in subsequent cardiac cycles, by delaying a next scheduled atrial pacing pulse if the next scheduled atrial pacing pulse is scheduled to occur when the atrial tissue is refractory; and
    - in response to a determination that the atrial depolarization occurred after the PVARP, using a pacemaker mediated tachyarrhythmia (PMT) management module to initiate PMT management, to avoid PMT in subsequent cardiac cycles, by extending a subsequent PVARP of the second cardiac cycle.

8. The system of claim 7, wherein the retrograde management module is configured to delay the next schedule atrial pacing pulse until about 300 ms from the atrial depolarization.

9. The system of claim 7, wherein extending the subsequent PVARP comprises extending the subsequent PVARP to about 500 ms.

10. The system of claim 7, wherein the atrial depolarization comprises a retrogradely conducted depolarization responsive to the ventricular pacing pulse.

11. The system of claim 7, wherein the atrial depolarization comprises a premature atrial contraction.

12. A cardiac rhythm management system, comprising:
- a pulse generator configured to deliver an atrial pacing pulse and a ventricular pacing pulse via electrodes coupled to a heart during a first paced cardiac cycle;
- a post ventricular atrial refractory period (PVARP) timer configured to time a PVARP following the ventricular pacing pulse;
- a capture detector configured to determine if the atrial pacing pulse captures the atrium;
- a sensing system;
- a controller coupled to the capture detector and the sensing system, the controller configured with:
  - (a) means for scheduling delivery of a second atrial pacing pulse in a second cardiac cycle that occurs next after the first paced cardiac cycle, in response to a determination that the atrial pacing pulse captured the atrium; and
  - (b) means for sensing an atrial depolarization occurring after delivery of the atrial and ventricular pacing pulses and determining whether such atrial depolarization occurs during or after the PVARP, in response to a determination that the atrial pacing pulse did not capture the atrium, comprising:
    - means for initiating retrograde management, to avoid retrograde conduction in subsequent cardiac cycles, by delaying a next scheduled atrial pacing pulse if the next scheduled pacing pulse is scheduled to occur when the atrial tissue is refractory, in response to a determination that the atrial depolarization occurred during the PVARP; and
    - means for initiating pacemaker mediated tachyarrhythmia (PMT) management, to avoid PMT in subsequent cardiac cycles, by extending a subsequent PVARP of the second cardiac cycle, in response to a determination that the atrial depolarization occurred after the PVARP.

13. The system of claim 12, further comprising means for delaying the next scheduled atrial pacing pulse until about 300 ms from the atrial depolarization.

* * * * *